United States Patent
Kitamura

(10) Patent No.: US 9,183,637 B2
(45) Date of Patent: Nov. 10, 2015

(54) IMAGE PROCESSING APPARATUS, METHOD, AND PROGRAM

(71) Applicant: FUJIFILM Corporation, Tokyo (JP)

(72) Inventor: Yoshiro Kitamura, Tokyo (JP)

(73) Assignee: Fujifilm Corporation, Tokyo (JP)

( * ) Notice: Subject to any disclaimer, the term of this patent is extended or adjusted under 35 U.S.C. 154(b) by 0 days.

(21) Appl. No.: 14/484,046

(22) Filed: Sep. 11, 2014

(65) Prior Publication Data

US 2015/0016686 A1 Jan. 15, 2015

Related U.S. Application Data

(63) Continuation of application No. PCT/JP2013/001636, filed on Mar. 13, 2013.

(30) Foreign Application Priority Data

Mar. 14, 2012 (JP) ................................. 2012-056855

(51) Int. Cl.
*G06T 7/00* (2006.01)
*A61B 5/00* (2006.01)

(52) U.S. Cl.
CPC ............. *G06T 7/0081* (2013.01); *G06T 7/0012* (2013.01); *G06T 7/0089* (2013.01); *G06T 7/0095* (2013.01); *A61B 5/489* (2013.01); *A61B 2576/00* (2013.01); *G06T 2207/10081* (2013.01); *G06T 2207/20024* (2013.01); *G06T 2207/20048* (2013.01); *G06T 2207/20056* (2013.01); *G06T 2207/20116* (2013.01); *G06T 2207/30101* (2013.01)

(58) Field of Classification Search
CPC combination set(s) only.
See application file for complete search history.

(56) References Cited

U.S. PATENT DOCUMENTS

| 6,342,886 | B1 * | 1/2002 | Pfister et al. | 345/424 |
| 6,448,968 | B1 * | 9/2002 | Pfister et al. | 345/423 |
| 2011/0026811 | A1 * | 2/2011 | Kameyama | 382/159 |

(Continued)

FOREIGN PATENT DOCUMENTS

| JP | 2011-104206 A | 6/2011 |
| JP | 2011-206531 A | 10/2011 |

OTHER PUBLICATIONS

International Search Report (ISR) (PCT Form PCT/ISA/210), in PCT/JP2013/001636, dated Jun. 18, 2013.

(Continued)

*Primary Examiner* — Anand Bhatnagar
(74) *Attorney, Agent, or Firm* — McGinn IP Law Group, PLLC

(57) ABSTRACT

An image processing apparatus, including a filtering unit that performs filtering on an image using a second order partial differential and calculates a Hessian matrix and an evaluation unit that discriminates a structure included in the image using eigenvalues and eigenvectors of the Hessian matrix, in which the filtering unit includes a correction unit that performs filtering on the image using a first order partial differential of a function representing a hollow sphere having the same radius as the radius of the solid sphere and obtains first order partial differential vectors, and carries out correction to cancel out one of response waveforms of the function representing the solid sphere in each direction, the response waveforms appearing at two positions symmetrically separated with respect to the center of the solid sphere, using values obtained by projecting the first order partial differential vectors onto directions of the eigenvectors.

15 Claims, 11 Drawing Sheets

(56) References Cited

U.S. PATENT DOCUMENTS

| | | | |
|---|---|---|---|
| 2011/0064289 A1* | 3/2011 | Bi et al. | 382/128 |
| 2011/0222748 A1* | 9/2011 | Kitamura | 382/128 |
| 2012/0157851 A1* | 6/2012 | Zwirn | 600/447 |
| 2014/0133271 A1* | 5/2014 | Sallas | 367/21 |

OTHER PUBLICATIONS

A. F. Frangi, et al., "Multiscale vessel enhancement filtering", Proceedings of MICCAI, vol. 1496, pp. 130-137, 1998.

M. Law and A. Chung, "Three Dimensional Curvilinear Structure Detection Using Optimally Oriented Flux", Proceedings of ECCV, Part IV, LNCS 5305, pp. 368-382, 2008.

Y. Y. Boykov and M. Jolly, "Interactive Graph Cuts for Optimal Boundary & Region Segmentation of Objects in N-D Images", Proceedings of "International Conference on Computer Vision", vol. I, pp. 105-112, 2001.

A. Kanitsar, et al., "CPR—Curved Planar Reformation", IEEE Visualization, 2002.

Z. Jin, et al., "Enhancement of Venous Vasculature in Susceptibility Weighted Images of the Brain Using Multi-Scale Vessel Enhancement Filtering", 2010 3rd International Conference on Biomedical Engineering and Information (BMEI 2010), pp. 226-230.

A. Oda, et al., "Development of a lymph node detection method from 3D abdominal CT images using multi shape ellipsoidal structure detection filter", IEICE Technical Report MI2011-123, pp. 251-256, 2012.

* cited by examiner

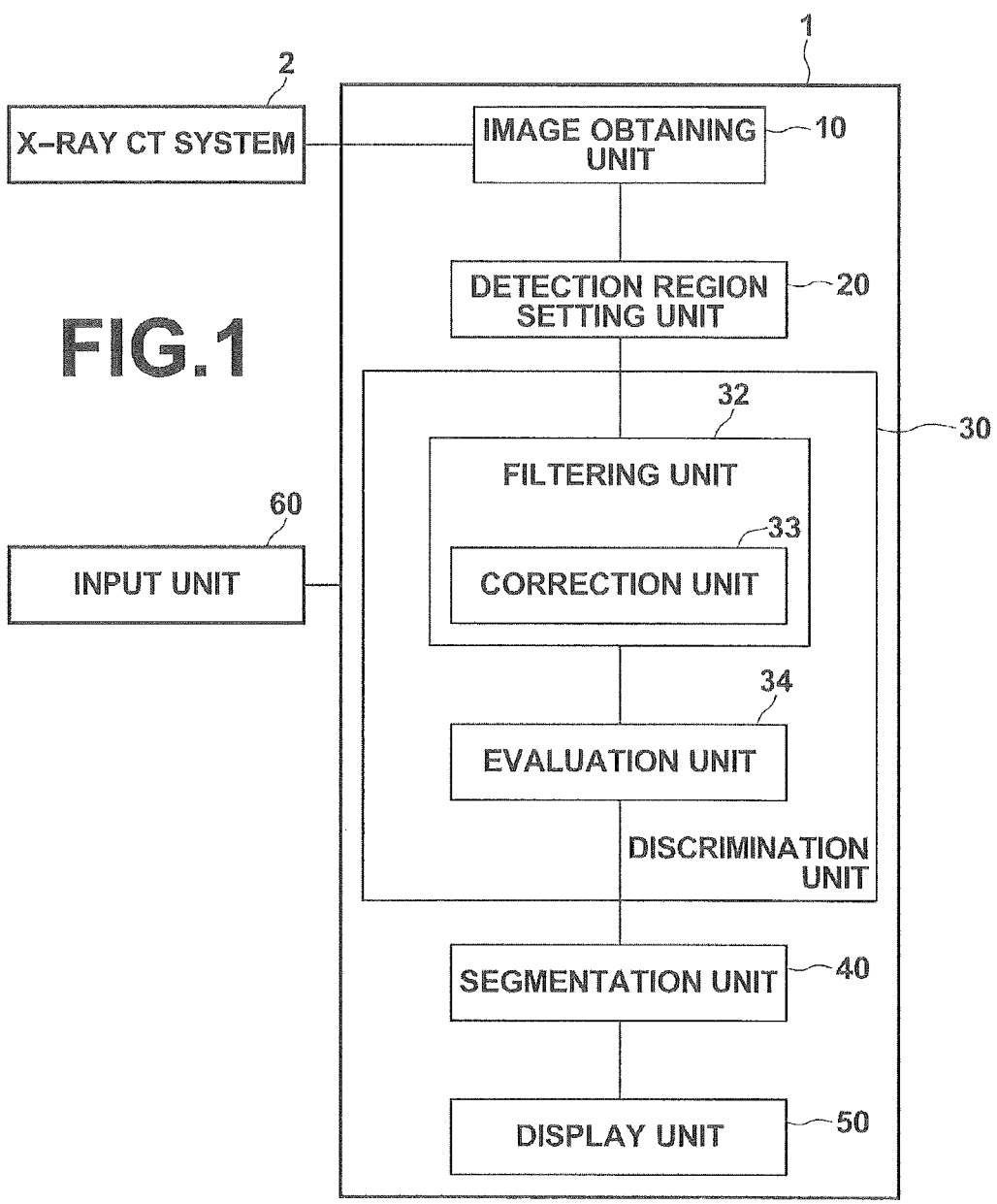
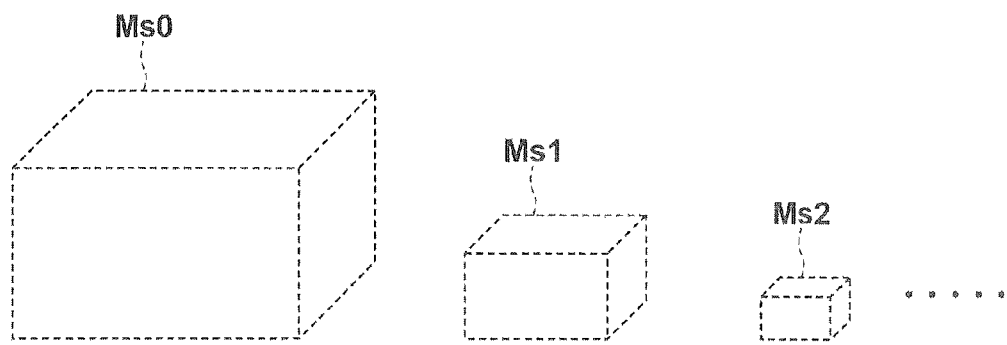

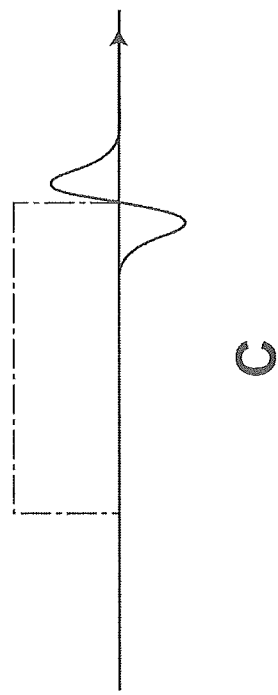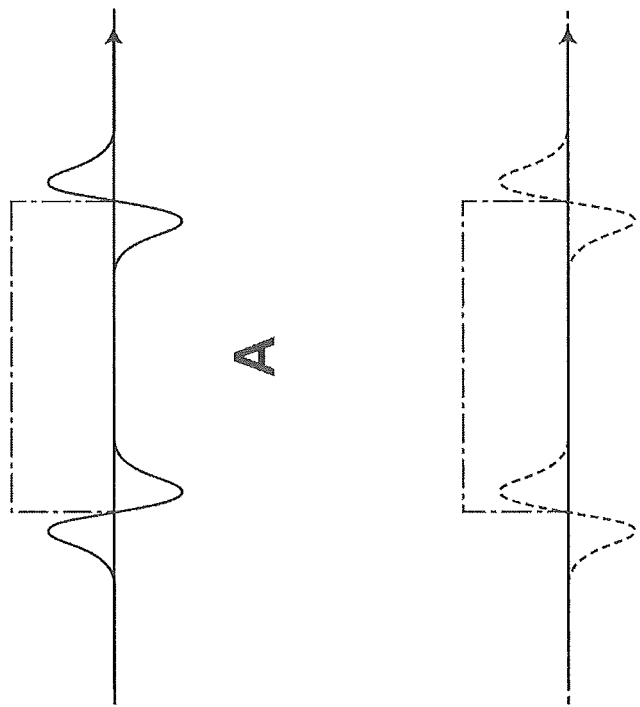

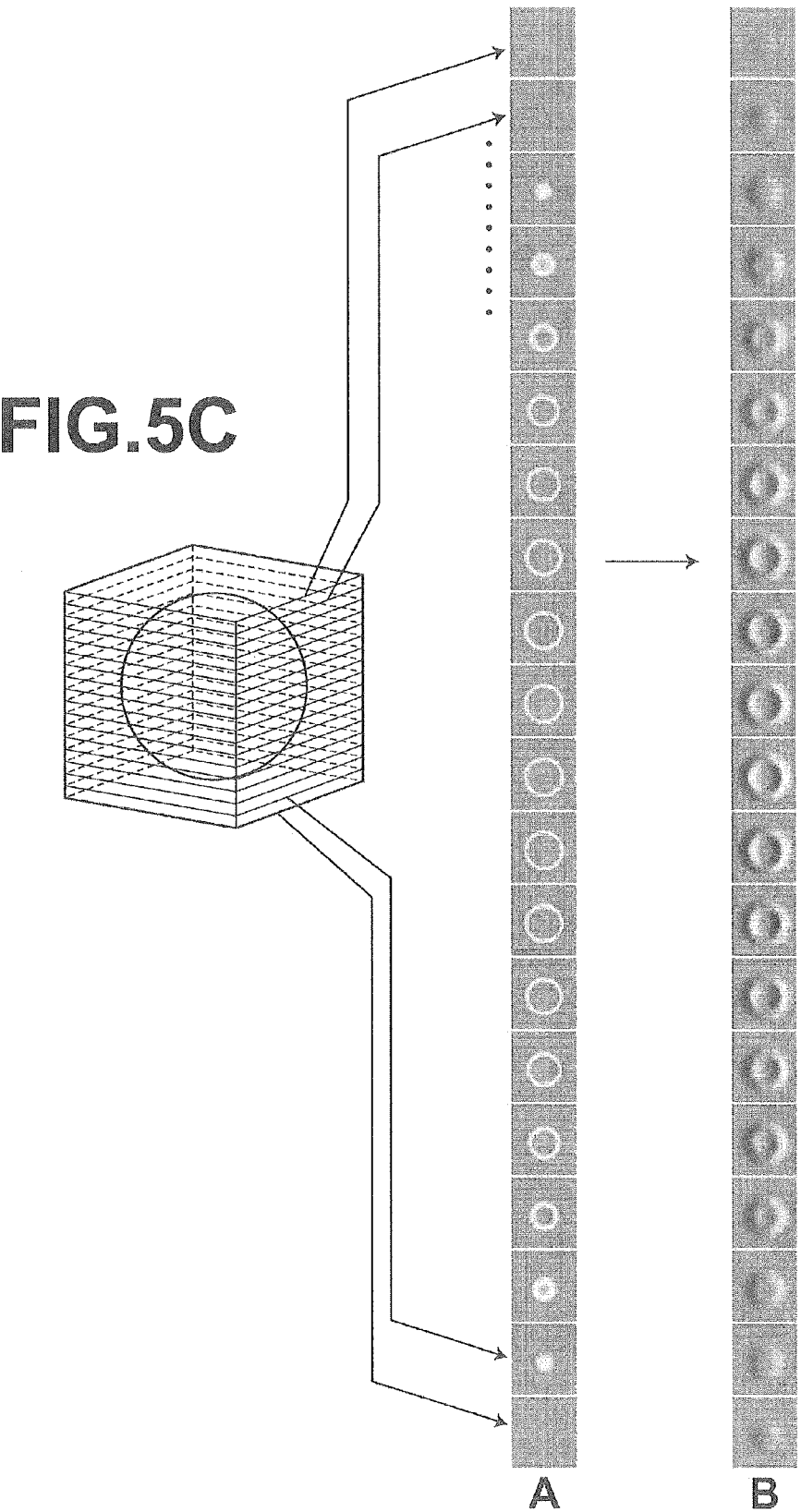

A      B      C      D

A      B      C      D

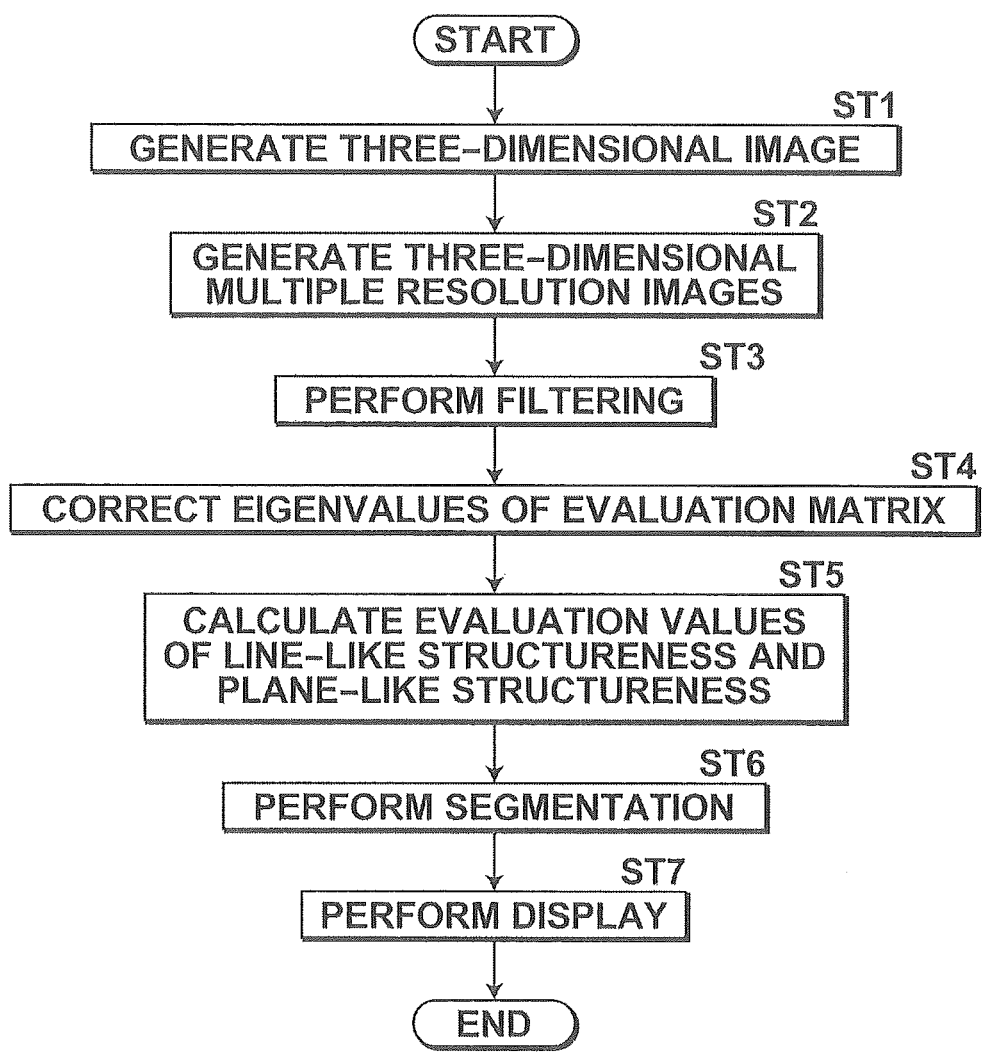

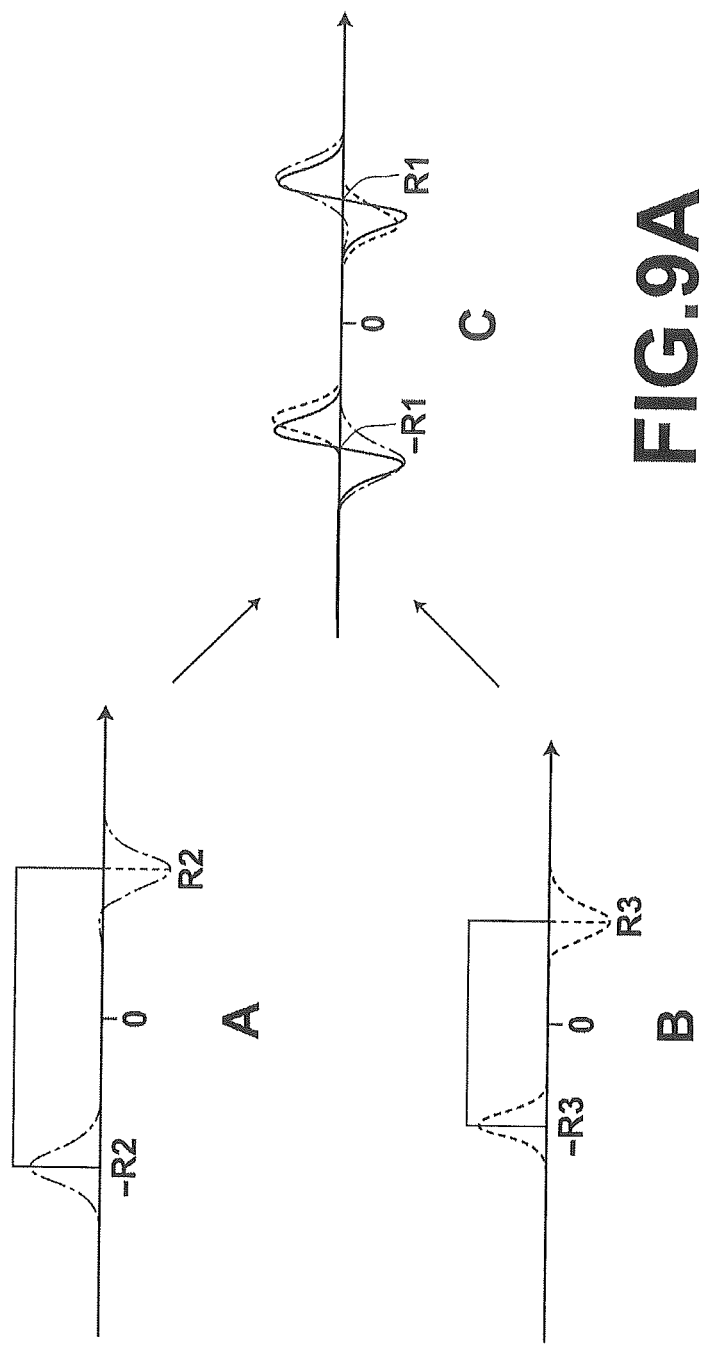

IMAGE PROCESSING APPARATUS, METHOD, AND PROGRAM

CROSS-REFERENCE TO RELATED APPLICATIONS

This application is a Continuation of PCT International Application No. PCT/JP2013/001636 filed on Mar. 13, 2013, which claims priority under 35 U.S.C. §119 (a) to Japanese Patent Application No. 2012-056855 filed on Mar. 14, 2012. Each of the above applications) is hereby expressly incorporated by reference in its entirety, into the present application.

TECHNICAL FIELD

The present invention relates to an image processing apparatus and method for discriminating structure of a structure in an image, and a program for causing a computer to perform the image processing method.

BACKGROUND ART

Recently, high quality three-dimensional images have been used in image diagnosis with the advancement of medical equipment (e.g., multidetector CT and the like). As a three-dimensional image is formed of a multiple of two-dimensional images and has a large amount of information, the doctor may sometimes require a prolonged time to find out a desired observation region and give a diagnosis. Consequently, it is practiced to extract an organ of interest and perform NIP, VR, or CPR display, or the like, in order to enhance the visibility of an entire organ or a lesion and improve efficiency of diagnosis.

In the meantime, as a method of extracting a blood vessel or a bone in a medical image, Hessian analysis using a Hessian matrix is proposed (refer to A. F. Frangi et al., "Multiscale vessel enhancement filtering", Proceedings of MICCAI, Vol. 1496, pp. 130-137, 1998). The Hessian analysis discriminates whether a local structure in an image is a point, a line, or a plane by analyzing eigenvalues of a Hessian matrix whose elements are second order partial differential coefficients calculated by the use of the second differential kernel of a given filter, such as Gaussian kernel or the like. The use of the Hessian analysis allows a blood vessel and a bone to be discriminated as a line-like structure and a plate-like structure respectively.

There are cases, however, in which, if another structure is present in the vicinity of a line-like structure (vicinity structure), the method of A. F. Frangi et al., "Multiscale vessel enhancement filtering", Proceedings of MICCAI, Vol. 1496, pp. 130-137, 1998 erroneously discriminates the vicinity structure as the line-like structure. The method of M. Law and A. Chung, "Three Dimensional Curvilinear Structure Detection Using Optimally Oriented Flux", Proceedings of ECCV, pp. 368-382, 2008 improves the filter proposed in A. F. Frangi et al., "Multiscale vessel enhancement filtering", Proceedings of MICCAI, Vol. 1496, pp. 130-137, 1998 by convoluting a function representing a solid sphere (solid sphere model function) with the inside of the spherical shape as 1 and the outside as 0 and limiting the calculation range of the second order partial differential coefficients to the surface of the sphere in Hessian analysis, whereby the influence of the vicinity structure on the filtering result may be reduced.

DISCLOSURE OF THE INVENTION

If a blood vessel, which is a line-like structure, is discriminated from a medical image that includes blood vessels of various thicknesses using the method of M. Law and A. Chung, "Three Dimensional Curvilinear Structure Detection Using Optimally Oriented Flux", Proceedings of ECCV, pp. 368-382, 2008, however, there may be a case in which a blood vessel narrower that an actual blood vessel is erroneously recognized inside a blood vessel. In other words, if a line-like structure is discriminated by the method of M. Law and A. Chung, "Three Dimensional Curvilinear Structure Detection Using Optimally Oriented Flux", Proceedings of ECCV, pp. 368-382, 2008, there may be a problem that an erroneous discrimination is made at a portion of the contour of a structure having a radius of curvature greater than radius of curvature of a solid sphere of a solid sphere model function that a line-like structure having a diameter substantially the same as the diameter of the solid sphere represented by the solid sphere model function is present.

The aforementioned problem may possibly occur at any contour portion of a structure having a radius of curvature greater than the radius of curvature of the solid sphere of the solid sphere model function. In view of the problem described above, therefore, it is an object of the present invention to prevent, in image processing method that performs filtering using a solid sphere model function in Hessian analysis, erroneous discrimination of structure that occurs at a contour portion of a structure having a radius of curvature greater than the radius of curvature of the solid sphere represented by the solid sphere model function.

An image processing apparatus according to the first invention includes a filtering unit that performs filtering on each pixel position in an image using a second order partial differential of a function representing a solid sphere and calculates a Hessian matrix, and an evaluation unit that discriminates a structure included in the image using eigenvalues and eigenvectors obtained by performing eigenvalue analysis on the calculated Hessian matrix, wherein the filtering unit includes a correction unit that performs filtering on each pixel position in the image using a first order partial differential of a function representing a hollow sphere having the same radius as the radius of the solid sphere and obtains first order partial differential vectors, and carries out correction to cancel out one of response waveforms of the second order partial differential of the function representing the solid sphere in each direction, the response waveforms appearing at two positions symmetrically separated with respect to the center of the solid sphere, using values obtained by projecting the obtained first order partial differential vectors onto directions of the eigenvectors.

An image processing method according to the first invention includes a filtering step that performs filtering on each pixel position in an image using a second order partial differential of a function representing a solid sphere and calculates a Hessian matrix, and an evaluation step that discriminates a structure included in the image using eigenvalues and eigenvectors obtained by performing eigenvalue analysis on the calculated Hessian matrix, wherein the filtering step performs filtering on each pixel position in the image using a first order partial differential of a function representing a hollow sphere having the same radius as the radius of the solid sphere and obtains first order partial differential vectors, and carries out correction to cancel out one of response waveforms of the second order partial differential of the function representing the solid sphere in each direction, the response waveforms appearing at two positions symmetrically separated with respect to the center of the solid sphere, using values obtained by projecting the obtained first order partial differential vectors onto directions of the eigenvectors.

Note that the image processing method according to the first invention may be provided as a program for causing a computer to perform the image processing method.

The "hollow sphere having the same radius as the radius of the solid sphere" as used herein includes not only the case where the radii of the solid sphere and the hollow sphere strictly corresponds to each other but also the case where the radius of the hollow structure is greater or smaller than the radius of the solid sphere if it is within the range having an effect of cancelling out the response waveform at one position of response waveforms of the second order partial differential of the function representing the solid sphere in each direction, the response waveforms appearing at two positions symmetrically separated with respect to the center of the solid sphere, using the first order partial differential vectors. In order to satisfactorily obtain the "effect of cancelling out the response waveform at one position", it is preferable that the radii of the hollow sphere and the solid sphere be equal as much as possible and, for example, the difference in radius between the hollow sphere and the solid sphere is preferably 20% or less and the difference in radius between the hollow sphere and the solid sphere is preferably 10% or less.

In the image processing apparatus according to the first invention, if eigenvalues of the evaluation matrix are taken as $\lambda_1, \lambda_2, \lambda_3$, eigenvectors are taken as $e_1=(x_1, y_1, z_1), e_2=(x_2, y_2, z_2) \, e_3=(x_3, y_3, z_3)$ and the first order partial differential vectors of the function representing the hollow sphere are taken as $(\rho_1, \rho_2, \rho_3)$, the correction unit carries out the correction to cancel out the one of the response waveforms by correcting the eigenvalues as shown in Formula (13) given below using $\rho_1', \rho_2', \rho_3'°$ calculated by Formula (12) given below and a predetermined coefficient:

$$\left.\begin{array}{l}\rho_1' = \rho_1 \times x_1 + \rho_2 \times y_1 + \rho_3 \times z_1 \\ \rho_2' = \rho_1 \times x_2 + \rho_2 \times y_2 + \rho_3 \times z_2 \\ \rho_3' = \rho_1 \times x_3 + \rho_2 \times y_3 + \rho_3 \times z_3\end{array}\right\} \quad (12)$$

$$\lambda_1' = \begin{cases} 0 & \text{if } |\lambda_1| < |\alpha\rho_1'| \\ \min(|\lambda_1 + \alpha\rho_1'|, |\lambda_1 - \alpha\rho_1'|) & \text{otherwise} \end{cases}$$

$$\lambda_2' = \begin{cases} 0 & \text{if } |\lambda_2| < |\alpha\rho_2'| \\ \min(|\lambda_1 + \alpha\rho_2'|, |\lambda_1 - \alpha\rho_2'|) & \text{otherwise} \end{cases} \quad (13)$$

$$\lambda_3' = \begin{cases} 0 & \text{if } |\lambda_3| < |\alpha\rho_3'| \\ \min(|\lambda_3 + \alpha\rho_3'|, |\lambda_1 - \alpha\rho_3'|) & \text{otherwise} \end{cases}$$

In the image processing apparatus according to the first invention, the function representing the hollow sphere is preferably represented by Formula (10) given below:

$$\left.\begin{array}{l} f(r) = \delta(r - R_4) \\ r = \sqrt{x^2 + y^2 + z^2} \end{array}\right\} \quad (10)$$

where, x, y, z are the coordinates of three-dimensional space, r is the polar coordinate representation thereof, and $R_4$ is the radius of the hollow sphere.

An image processing apparatus according to the second invention includes a filtering unit that performs filtering on each pixel position in an image using a second order partial differential of a function representing a first solid sphere and calculates a Hessian matrix, and an evaluation unit that discriminates a structure included in the image using eigenvalues and eigenvectors obtained by performing eigenvalue analysis on the calculated Hessian matrix, wherein the filtering unit includes a correction unit that performs filtering on each pixel position in the image using a first order partial differential of a function representing a second solid sphere having a second radius greater than a first radius which is the radius of the first solid sphere and calculates first order partial differential vectors, further performs filtering on each pixel position in the image using a first order partial differential of a function representing a third solid sphere having a third radius which is smaller than the first radius and calculates first order partial differential vectors, and carries out correction to cancel out a response waveform at one position of response waveforms of the second order partial differential of the function representing the first solid sphere in each direction, the response waveforms appearing at two positions symmetrically separated with respect to the center of the first solid sphere, using values obtained by projecting the first order partial differential vectors of the function representing the second solid sphere onto directions of the eigenvectors and values obtained by projecting the first order partial differential vectors of the function representing the third solid sphere onto directions of the eigenvectors.

Preferably, in the image processing apparatus according to the second invention, the response waveform at the one position is a waveform in which one positive peak and one negative peak are adjoining to each other, the second radius corresponds to the length from the center of the solid sphere to the positive peak or the length from the center of the solid sphere to the negative peak, whichever is longer, and the third radius corresponds to the length from the center of the solid sphere to the positive peak or the length from the center of the solid sphere to the negative peak, whichever is shorter.

The "the second radius corresponds to the length from the center of the first solid sphere to the positive peak or the length from the center of the first solid sphere to the negative peak, whichever is longer" includes not only the case where the second radius corresponds strictly to the length from the center of the first solid sphere to the positive peak or the length from the center of the first solid sphere to the negative peak, whichever is longer (first length), but also the case where the second radius is greater or smaller than the first length if it is within the range having an effect of cancelling out the response waveform at one position of response waveforms of the second order partial differential of the function representing the first solid sphere in each direction, the response waveforms appearing at two positions symmetrically separated with respect to the center of the solid sphere, using the vectors obtained by weighting the first order partial differential vectors of the function representing the second solid sphere and the vectors obtained by weighting the first order partial differential vectors of the function representing the third solid sphere. In order to satisfactorily obtain the "effect of cancelling out the response waveform at one position", it is preferable that the second radius and the first length be equal as much as possible and, for example, the difference between the second radius and the first length is preferably 20% or less and more preferably 10% or less.

Likewise, the "the third radius corresponds to the length from the center of the first solid sphere to the positive peak or the length from the center of the first solid sphere to the negative peak, whichever is shorter" includes not only the case where the third radius corresponds strictly to the length from the center of the first solid sphere to the positive peak or the length from the center of the first solid sphere to the negative peak, whichever is shorter (second length), but also the case where the third radius is greater or smaller than the second length if it is within the range having an effect of cancelling out the response waveform at one position of response waveforms of the second order partial differential of the function representing the first solid sphere in each direction, the response waveforms appearing at two positions symmetrically separated with respect to the center of the solid sphere, using the vectors obtained by weighting the first order partial differential vectors of the function representing the second solid sphere and the vectors obtained by weighting the first order partial differential vectors of the function representing the third solid sphere. In order to satisfactorily obtain the "effect of cancelling out the response waveform at one position", it is preferable that the third radius and the second length be equal as much as possible and, for example, the difference between the third radius and the second length is preferably 20% or less and more preferably 10% or less.

In the image processing apparatus according to the first invention, the filtering unit preferably calculates, with respect to functions representing the solid sphere in a plurality of sizes, an evaluation matrix by performing filtering with a second order partial differential matrix of a function representing each solid sphere.

In the image processing apparatus according to the second invention, the filtering unit calculates, with respect to functions representing the first solid sphere in a plurality of sizes, an evaluation matrix by performing filtering with a second order partial differential matrix of a function representing each of the first solid spheres.

Preferably, in the image processing apparatuses according to the first and the second inventions, the image is a medical image and the structure is a blood vessel.

Preferably, in the image processing apparatuses according to the first and the second inventions, the filtering unit performs the filtering using the second order partial differential matrix of the function representing the solid sphere in Fourier space.

Preferably, in the image processing apparatuses according to the first and the second inventions, the evaluation unit discriminate at least one of local point-like, line-like, and plane-like structures of the structural object.

According to the first invention, a filtering unit that performs filtering on each pixel position in an image using a second order partial differential of a function representing a solid sphere and calculates a Hessian matrix, and an evaluation unit that discriminates a structure included in the image using eigenvalues and eigenvectors obtained by performing eigenvalue analysis on the calculated Hessian matrix are provided, and the filtering unit includes a correction unit that performs filtering on each pixel position in the image using a first order partial differential of a function representing a hollow sphere having the same radius as the radius of the solid sphere and obtains first order partial differential vectors, and carries out correction to cancel out one of response waveforms of the second order partial differential of the function representing the solid sphere in each direction, the response waveforms appearing at two positions symmetrically separated with respect to the center of the solid sphere, using values obtained by projecting the obtained first order partial differential vectors onto directions of the eigenvectors. This may inhibit erroneous discrimination that occurs when a contour portion of a structure having a radius of curvature greater than the radius of curvature of a solid sphere of a function representing the solid sphere corresponds to only one position of response waveform of the second partial differential of the function representing the solid sphere in each direction and the accuracy of the evaluation values may be improved. Consequently, a structure included in an image may be discriminated more accurately based on the evaluation values.

According to the second invention, a filtering unit that performs filtering on each pixel position in an image using a second order partial differential of a function representing a solid sphere and calculates a Hessian matrix, and an evaluation unit that discriminates a structure included in the image using eigenvalues and eigenvectors obtained by performing eigenvalue analysis on the calculated Hessian matrix are provided, and the filtering unit includes a correction unit that performs filtering on each pixel position in the image using a first order partial differential of a function representing a second solid sphere having a second radius which is greater than a first radius, the first radius being the radius of the first solid sphere, and calculates first order partial differential vectors, further performs filtering on each pixel position in the image using a first order partial differential of a function representing a third solid sphere having a third radius which is smaller than the first radius and calculates first order partial differential vectors, and carries out correction to cancel out a response waveform at one position of response waveforms of the second order partial differential of the function representing the solid sphere in each direction, the response waveforms appearing at two positions symmetrically separated with respect to the center of the solid sphere, using values obtained by projecting the first order partial differential vectors of the function representing the second solid sphere onto directions of the eigenvectors and values obtained by projecting the first order partial differential vectors of the function representing the third solid sphere onto directions of the eigenvectors. This may inhibit erroneous discrimination that occurs when a contour portion of a structure having a radius of curvature greater than the radius of curvature of a solid sphere of a function representing the solid sphere corresponds to only one position of response waveform of the second partial differential of the function representing the solid sphere in each direction and the accuracy of the evaluation values may be improved. Consequently, a structure included in an image may be discriminated more accurately based on the evaluation values.

BRIEF DESCRIPTION OF DRAWINGS

FIG. 1 is a schematic block diagram of an image processing apparatus according to a first embodiment of the present invention, illustrating a configuration thereof.

FIG. 2 is a drawing for explaining a multiple resolution transformation.

FIG. 5A is a drawing for explaining the principle of correction processing according to the first embodiment of the present invention.

FIG. 5C is a drawing for explaining response of first order partial differential of a hollow sphere model function in x direction used for correction processing of the first embodiment of the present invention.

FIG. 7 is a flowchart of processing performed in the first embodiment of the present invention.

FIG. 9A is a drawing for explaining the principle of correction processing according to a second embodiment of the present invention.

BEST MODE FOR CARRYING OUT THE INVENTION

Figure 3:
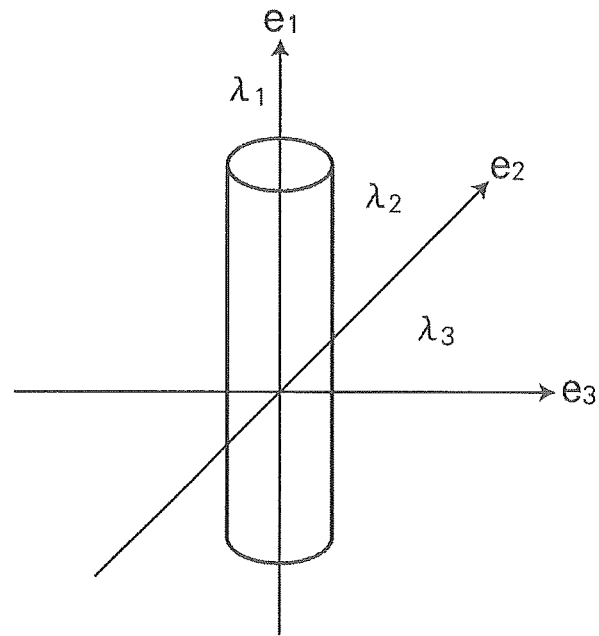
FIG. 3 is a drawing for explaining eigenvalues of a line-like structure.

Hereinafter, embodiments of the present invention will be described with reference to the accompanying drawings. FIG. 1 is a schematic block diagram of an image processing apparatus according to an embodiment of the present invention, illustrating a configuration thereof. The configuration of the image processing apparatus 1 shown in FIG. 1 is realized by executing a program read into an auxiliary storage (not shown) on a computer (e.g., personal computer). The program is provided being recorded on an information storage medium, such as CD-ROM and the like, or distributed via a network, such as the Internet, and installed on a computer.

The image processing apparatus 1 generates a three-dimensional image M0 using a plurality of two-dimensional images captured, for example, by an X-ray CT system 2 and automatically segments a line-like structure and a plate-like structure included in the three-dimensional image M0. The image processing apparatus 1 includes an image obtaining unit 10, a detection region setting unit 20, a discrimination unit 30, a segmentation unit 40, a display unit 50, and an input unit 60.

The image obtaining unit 10 obtains a plurality of CT images (two-dimensional images) captured, for example, by the X-ray CT system 2, and generates a three-dimensional image M0 from the plurality of two-dimensional images. The image obtaining unit 10 may be a unit that obtains two-dimensional images, such as so-called MRI images, RI images, PET images, X-ray images, and the like, as well as CT images.

The detection region setting unit 20 first makes the voxel dimensions of the three-dimensional image M0 isotropic. For example, if the voxel dimensions of the three-dimensional image M0 are 0.3 mm, 0.3 mm, and 0.6 mm in the X, Y, and Z directions of the three-dimensional image M0 respectively, they are made isotropic to (X,Y,Z)=(0.5, 0.5, 0.5) (mm).

The detection region setting unit 20 performs a multiple resolution transformation on the three-dimensional image M0 after making the image isotropic and generates a plurality of three-dimensional multiple resolution images Msi (i=0 to n) (Gaussian pyramid) as shown in FIG. 2. Note that i=0 represents the same resolution as the resolution of the three-dimensional image M0 and i=n represents the lowest resolution. The image is reduced by the increments of √2 and the voxel dimensions of the three-dimensional multiple resolution images Msi are (X, Y, Z)=(0.5, 0.5, 0.5), (0.7, 0.7, 0.7), (1.0, 1.0, 1.0), and so on in descending order of resolution.

The discrimination unit 30 includes a filtering unit 32, a correction unit 33, and an evaluation unit 34. The filtering unit 32 performs filtering, which is identical to the filtering of the method of M. Law and A. Chung, "Three Dimensional Curvilinear Structure Detection Using Optimally Oriented Flux", Proceedings of ECCV, pp. 368-382, 2008, on each of the three-dimensional multiple resolution images Msi using a function representing a solid sphere to be described later (solid sphere model function) and a Gaussian kernel in order to perform Hessian analysis using a Hessian matrix (evaluation matrix). That is, a filter kernel of the same size is convoluted with each of the multiple resolution images Msi having different resolutions. The solid sphere model function is defined by the radius R of the solid sphere and "σ" of the Gaussian kernel. For these, appropriate values are set based on the knowledge acquired by preliminary analysis and the like. For the radius R of the solid sphere, a value which is at least greater than "σ" of the Gaussian kernel is set.

By convoluting the filter kernel of the same size (e.g., R=2.0 (voxels), σ=0.5 (voxels)) with each of the three-dimensional multiple resolution images Msi, filter kernels of different sizes are applied, in effect, to the three-dimensional image M0, so that a point-like structure, a line-like structure (e.g., blood vessel), and a plate-like structure (e.g., cortical bone) having different sizes may be detected. In other words, functions representing solid sphere with radius R in a plurality of sizes are used, and an evaluation matrix is calculated by performing filtering using a second order partial differential matrix of a function representing each solid sphere.

The Hessian analysis using a second order partial differential of the solid sphere model function of M. Law and A. Chung, "Three Dimensional Curvilinear Structure Detection Using Optimally Oriented Flux", Proceedings of ECCV, pp. 368-382, 2008 will be described. The Hessian matrix used for the Hessian analysis is a 3×3 matrix for the three-dimensional image, as indicated in Formula (1) given below.

$$\nabla^2 I = \begin{bmatrix} Ixx & Ixy & Ixz \\ Iyx & Iyy & Iyz \\ Izx & Izy & Izz \end{bmatrix} \quad (1)$$

$$Ixx = \frac{\partial^2 I}{\partial x^2},$$

$$Ixy = \frac{\partial^2 I}{\partial x \partial y}, \ldots$$

Each of the elements of the aforementioned Hessian matrix Ixx, Ixy, Iyy, Iyz, Izz, Izx is calculated by performing filtering (convolution operation) on the image data of a target image using second order partial differential of a hollow sphere model function f(r) and a Gaussian kernel function g(r).

In M. Law and A. Chung, "Three Dimensional Curvilinear Structure Detection Using Optimally Oriented Flux", Proceedings of ECCV, pp. 368-382, 2008, the filtering processing is performed in Fourier space. First, the image data of a target image are Fourier transformed. Then, the Fourier transformed target image (FT (image)) is multiplied by the solid sphere model function, the Gaussian kernel function, and the second order partial differential, each being Fourier transformed. Then, by performing a reverse Fourier transform on the multiplication result, the filtering result is obtained. Note that the obtained filtering result is the same as the filtering result obtained by performing a convolution operation in real space. If the Fourier transform of the solid sphere model function is taken as F(v) and the Fourier transform of the Gaussian kernel function is taken as G(v), the above relationship may be represented by Formula (2) given below.

$$FT^{-1}(FT(\text{image}) \times F(v) \times G(v) \times (2\pi v_x)^l \times (2\pi v_x)^m \times (2\pi v_z)^n) \quad (2)$$

$$G(v) = \exp\left(-\frac{v^2 \sigma^2}{2}\right) \quad (3)$$

$$v = \sqrt{v_x^2 + v_y^2 + v_z^2} \quad (4)$$
$$F(v) = \frac{4\pi \sin(av) - 4\pi av \cos(av)}{v^3}$$

$$r = \sqrt{x^2 + y^2 + z^2} \quad (5)$$
$$f(r) = \begin{cases} 1, & \text{if } r \le R \\ 0, & \text{otherwise} \end{cases}$$

where, x, y, z are the three-dimensional axes in real space, and R is the radius of the solid sphere. The polar coordinate representation of the variable (frequency) of the three-dimensional Fourier space is expressed as $v = (v_x^2 + v_y^2 + v_z^2)^{1/2}$ as indicated in Formula (4).

With respect to each function used in Formula (2), the Fourier transformed Gaussian kernel G(v) is shown in Formula (3) above and the solid sphere model function F) is shown in Formula (4) above. The solid sphere model function F(v) shown in Formula (4) may be obtained by Fourier transforming the function F(r) representing a solid sphere shown in Formula (5). The Gaussian kernel function G(v) shown in Formula (3) is used to define the differential range of pixel values of the target image, as in A. F. Frangi et al., "Multiscale vessel enhancement filtering", Proceedings of MICCAI, Vol. 1496, pp. 130-137, 1998 and M. Law and A. Chung, "Three Dimensional Curvilinear Structure Detection Using Optimally Oriented Flux", Proceedings of ECCV, pp. 368-382, 2008.

In Formula (2), the part $(2\pi v_x)^l \times (2\pi v_y)^m \times (2\pi v_z)^n$ corresponds to the differential processing in Fourier space and a value corresponding to each of the elements Ixx, Ixy, Iyy, Iyz, Izz, and Izx may be calculated by assigning coefficients l, m, and n corresponding to the respective differential directions in Formula (4) such that l+m+n=2 (0<l, 0<m, 0<n). For example, the element Ixx which is a second order partial differential value in x direction in the Hessian matrix at a processing target pixel of the three-dimensional multiple resolution images Msi may be calculated by assigning l=2 in x direction and m=n=0 in Y and Z directions in Formula (2). Further, the element Ixy in the Hessian matrix at a processing target pixel of the three-dimensional multiple resolution images Msi may be calculated by assigning l=m=1 in X and Y directions and n=0 in Z direction in Formula (2).

When eigenvalues are obtained by applying eigenvalue decomposition to the Hessian matrix calculated in the manner described above, it is known that a line-like structure has characteristics that two of the three eigenvalues are relatively large while the remaining one is close to 0, as shown in FIG. 3. For example, eigenvalues of Formula (1) have the relationship of Formula (6) with a target tissue of a line-like structure. It is assumed that the eigenvalues are $|\lambda_1| \le |\lambda_2| \le |\lambda_3|$.

$$\text{Eigenvalues of } \nabla^2 I: \lambda_1, \lambda_2, \lambda_3 \quad (6)$$
$$\begin{rcases} \lambda 1 \approx 0 \\ \lambda 2 >> 0 \\ \lambda 3 >> 0 \end{rcases}$$

Figure 4:
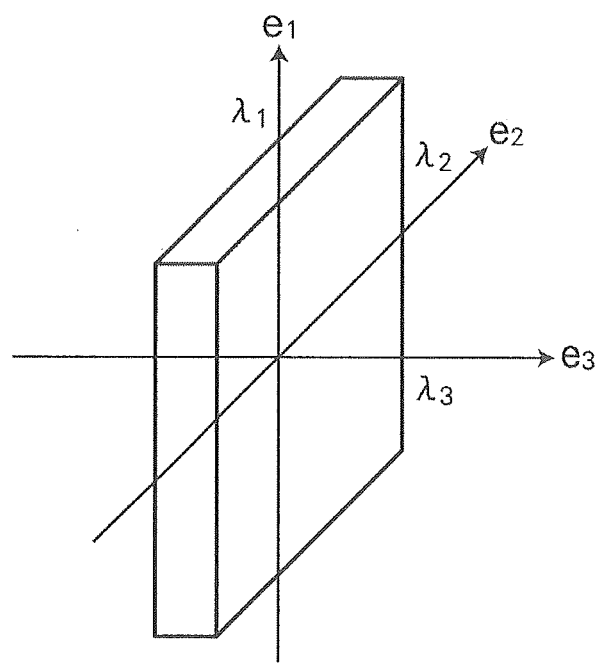
FIG. 4 is a drawing for explaining eigenvalues of a plane-like structure.

Further, it is known that a plate-like structure has characteristics that one of the three eigenvalues is large while the remaining two are close to 0, as shown in FIG. 4. For example, eigenvalues of Formula (1) have the relationship of Formula (7) with a target tissue of a plate-like structure.

$$\begin{rcases} \lambda 1 \approx 0 \\ \lambda 2 \approx 0 \\ \lambda 3 >> 0 \end{rcases} \quad (7)$$

Still further, it is known that a point-like structure has characteristics that all three eigenvalues are large. For example, eigenvalues of Formula (1) have the relationship of Formula (8) with a target tissue of a point-like structure.

$$\begin{rcases} \lambda 1 >> 0 \\ \lambda 2 >> 0 \\ \lambda 3 >> 0 \end{rcases} \quad (8)$$

Therefore, line-like structureness, plane-like structureness, and point-like structureness may be discriminated from the eigenvalues, and a blood vessel region which is a line-like structure and a bone region which is a plate-like structure may be segmented in the three-dimensional image M0 using the discrimination results.

The correction section 33 in the present embodiment applies eigenvalue decomposition to the Hessian matrix calculated by the filtering unit 32 and calculates three eigenvalues $\lambda_1, \lambda_2, \lambda_3$ ($|\lambda_1| \le |\lambda_2| \le |\lambda_3|$).

Here, the principle of inhibiting erroneous discrimination according to the present embodiment will be described using FIGS. 5A, 5B, 5C, 5D and specific correction processing by the correction section 33 based on the principle will be described thereafter.

FIG. 5A shows a solid sphere model function (dash-dot line) and a response of the second order partial differential (solid line) of the solid sphere model function at each x position in x direction in A, a hollow sphere model function (dash-dot line) and a response of the first order partial differential (broken line) of the hollow sphere model function at each x position in x direction in B, and a solid sphere model function and a response of the second order partial differential of the solid sphere model function at each x position in x direction corrected using the first order partial differential of the solid sphere model function in C.

As illustrated in A of FIG. 5A, the second order partial differential of the solid sphere model function in each direction shows response waveforms at two separate positions corresponding to the surface of the solid sphere. If a line segment traversing a structure, such as the diameter of a blood vessel or the like, corresponds to the diameter of the solid sphere represented by the solid sphere model function, two opposite portions of the contour of a structure (both ends of a line segment traversing the structure) in an image correspond respectively to the two positions where the aforementioned response waveforms of the second order partial differential of the solid sphere model function are indicated in each differential direction and large responses (expected responses) may be obtained. Thus, according to the Hessian analysis of the method of M. Law and A. Chung, "Three Dimensional Curvilinear Structure Detection Using Optimally Oriented Flux", Proceedings of ECCV, pp. 368-382, 2008, a structure, such as a blood vessel and the like, may be discriminated.

In the meantime, if only one position of the response waveform of the second order partial differential of the solid sphere model function in each differential direction corresponds to a contour portion of a structure larger in radius of curvature than the solid sphere in an image, a response of a given magnitude corresponding to the response of the one position can be obtained. The present inventor has presumed that it is a cause of the erroneous discrimination of a structure having substantially the same diameter as the diameter of the solid sphere that no distinction cannot be made between the response having a given magnitude and the expected response. Then, the present inventor has found out that the erroneous discrimination can be eliminated by cancelling out the response waveform at one position of the second order partial differential of the solid sphere model function in each direction. Then, as illustrated in A of FIG. 5A, the second order partial differential of the solid sphere model function in each direction has characteristics that it shows response waveforms at two positions symmetrical with respect to the center. Thus, the present inventor has paid attention to cancel out the response waveform at one position of the second order partial differential matrix of the solid sphere model function by the use of a function having a response waveform substantially identical in shape to the one response waveform with a reversed positive/negative sign at the same position as the position of the one response waveform of the second order partial differential of the solid sphere model function.

The present embodiment utilizes the fact that the response of first order partial differential of a hollow sphere model function $f_1(r)$ of the same size as the size of the solid sphere in x direction has characteristics that it has a response waveform having a substantially identical shape to the shape of one response waveform of the solid sphere model function with the same positive/negative sign at the same position as the position of the one of the response waveforms of the second order partial differential of the solid sphere model function in x direction and a response waveform having a substantially identical shape to the shape of the other response waveform of the solid sphere model function with a reversed positive/negative sign at the same position as the position of the other waveform of the second order partial differential of the solid sphere model function in x direction, as illustrated in B of FIG. 5A, and a first order partial differential value of the hollow sphere model function $f_1(r)$ of the same size as the size of the solid sphere in x direction is used to cancel out the response waveform at one position of the second order partial differential of the solid sphere model in x direction.

That is, addition of the response of the filtering using the second order partial differential of the solid sphere model function in x direction and the response of the filtering using the first order partial differential of the hollow sphere model function representing the hollow sphere having substantially the same radius as the radius of the solid sphere represented by the solid sphere model function will result in that the response waveforms on the negative side in x direction are cancelled out as they have reverse signs at the same position and the response waveforms on the positive side in x direction are reinforced as they have the same sign at the same position, and a response waveform appears only one position on the positive side in x direction, as shown in C of FIG. 5A.

Figure 5B:
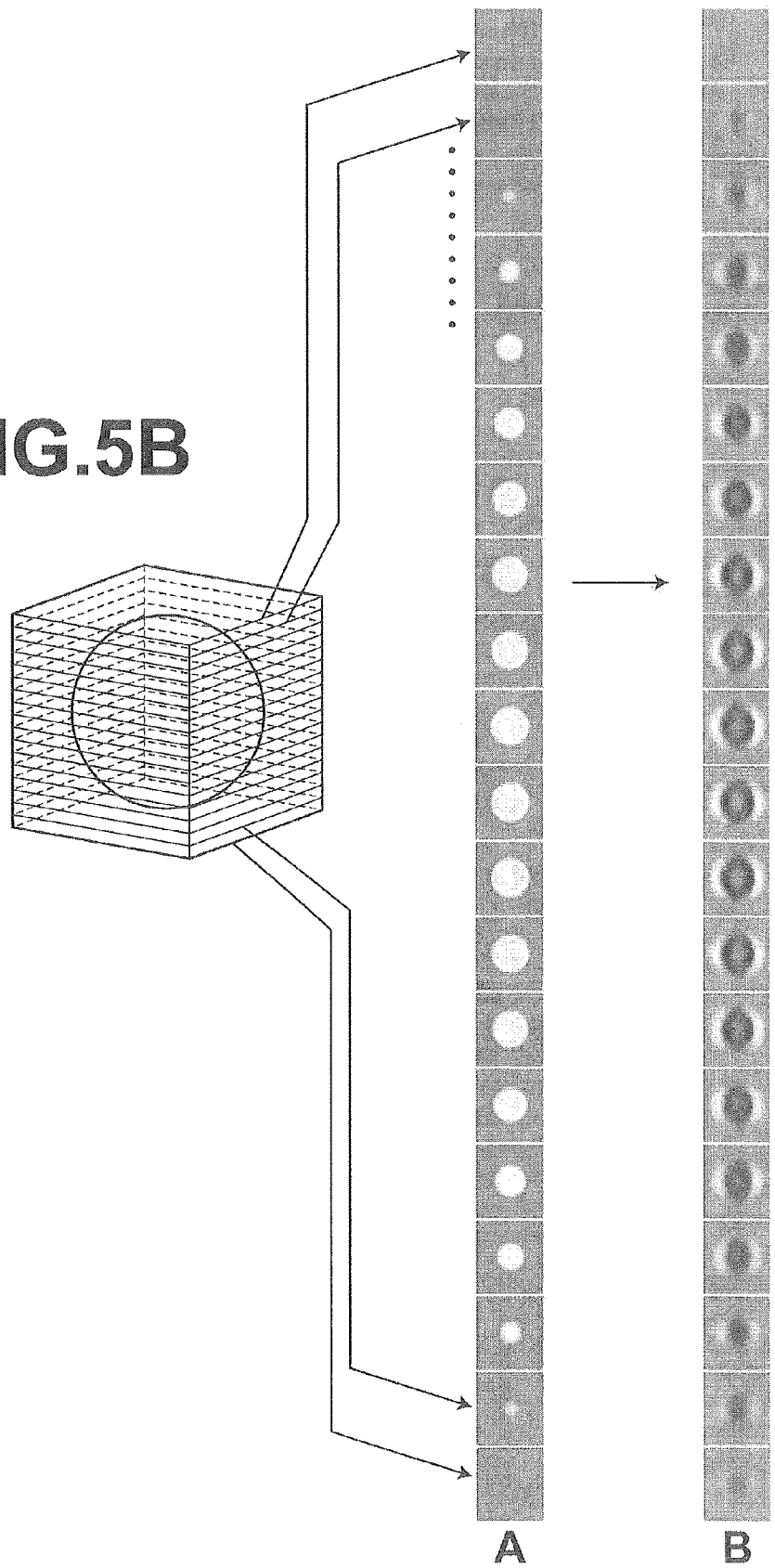
FIG. 5B is a drawing for explaining response of second order partial differential of a solid sphere model function in x direction used for filtering of the first embodiment of the present invention.
Figure 5D:
FIG. 5D is a drawing for explaining the response of the second order partial differential of the solid sphere in x direction corrected by the first order partial differential of the hollow sphere model function of the first embodiment of the present invention.

A of FIG. 5B shows a solid sphere model function f(r) and B shows a response of the second order partial differential of the solid sphere model function f(r) in x direction. A of FIG. 5C shows a hollow sphere model function $f_1(r)$ and B shows a response of the first order partial differential of the hollow sphere model function $f_1(r)$ in x direction. FIG. 5D shows a result of the addition of the response of the second order partial differential of the solid sphere model function shown in B of SB and the response of the first order partial differential of the hollow sphere model function $f_1(r)$ shown in FIG. 5C. In FIGS. 5B to D, each response described above is shown by a plurality of x-y plan views having different z coordinate values of equal intervals, and the plurality of x-y plan views is arranged in descending order of z coordinate values from the top in the vertical direction.

In the x-y plan views representing each response, the higher (whiter) the brightness, the greater the response in the positive direction and the darker (blacker) the brightness, the greater the response in the negative direction. The response waveform of the adjoining positive peak and negative peak located on the negative side of the center of the solid sphere shown in B of FIG. 5B and the response waveform of the adjoining negative peak and positive peak located on the negative side of the center of the solid sphere shown in B of FIG. 5C mutually cancel out, and it is known that no response waveform appears on the negative side of the center of the solid sphere in FIG. 5D. Likewise, the response waveform on the negative side of the center of the solid sphere may be cancelled out in each direction.

In the present invention, the correction unit 33 corrects eigenvalues of the Hessian matrix using a first order partial differential vectors of the hollow sphere model function such that the response waveform at one position of the solid sphere model function f(r) in each direction is cancelled out based on the aforementioned principle. A specific correction method will be described hereinafter.

In the present embodiment, the correction section 33 first calculates first order partial differential vectors to be used for correction using Formula (9). More specifically, as shown in Formula (9), a Fourier transformed Gaussian kernel function G(v) and a first order partial differential filter of a Fourier transformed hollow sphere mode function $F_1(v)$ shown in Formula (11) are convoluted with a processing target pixel of a Fourier transformed three-dimensional multiple resolution images Msi, and the first order partial differential vectors to be used for the eigenvalue correction of the Hessian matrix are calculated by performing reverse Fourier transform of the filtering result. Here, the hollow sphere model function $f_1(v)$ used in Formula (11) may be obtained by performing Fourier transform on the hollow sphere model function f(r) defined by the delta function $\delta(r-R_4)$ represented by Formula (10).

$$FT^{-1}(FT(\text{image}) \times F_1(v) \times G(v) \times (2\pi v_x)^l \times (2\pi v_y)^m \times (2\pi v_z)^n) \quad (9)$$

$$\left. \begin{array}{l} f_1(r) = \delta(r - R_4) \\ r = \sqrt{x^2 + y^2 + z^2} \end{array} \right\} \quad (10)$$

$$\left. \begin{array}{l} F_1(v) = \dfrac{\sin(R_4 v)}{R_4 v} \\ v = \sqrt{v_x^2 + v_y^2 + v_z^2} \end{array} \right\} \quad (11)$$

In Formula (9), the part $(2\pi v_x)^l \times (2\pi v_y)^m \times (2\pi v_z)^n$ corresponds to the differential processing in Fourier space and a value corresponding to each of the elements $\rho_1$, $\rho_2$, $\rho_3$ of the first order partial differential vectors may be calculated by assigning coefficients l, m, n corresponding to the respective differential directions in Formula (9) such that l+m+n=1 (0<l, 0<m, 0<n).

In Formula (9), the filtering is performed in Fourier space, but the filtering may be performed in real space. In Formula (10), x, y, z are coordinates of three-dimensional space, r is the polar coordinate representation thereof, and $R_4$ is the radius of the hollow sphere. In the present embodiment, the radius $R_4$ of the hollow sphere represented by the hollow sphere model function is the same as the radius R of the solid sphere represented by the solid sphere model function. Note that the radius $R_4$ of the hollow sphere may be larger or smaller than the radius R of the solid sphere within the range having an effect of cancelling out the response waveform at one position of the second order partial differential of the solid sphere model function, but it is preferable that the radius $R_4$ corresponds strictly to the radius R of the solid sphere in order to make the response waveform of the first order differential of the hollow sphere model function correspond more to the response waveform at one position of the second order partial differential of the solid sphere model function.

As the first order partial differential vectors $(\rho_1, \rho_2, \rho_3)$ of X direction, Y direction, and Z direction calculated in the manner described above are deviated from the directions of the eigenvectors $e_1$, $e_2$, $e_3$ of the eigenvalues $\lambda_1$, $\lambda_2$, $\lambda_3$, the correction unit 33 calculates first order partial differential vectors $\rho_1'$, $\rho_2'$, $\rho_3'$ corresponding to the directions of the eigenvectors $e_1$, $e_2$, $e_3$ by Formula (12) given below. Note that, eigenvectors of the evaluation matrix is taken as $e_1=(x_1, y_1, z_1)$ $e_2=(x_2, y_2, z_2)$, $e_3=(x_3, y_3, z_3)$ and the first order partial differential vectors of the function representing the hollow sphere are taken as $(\rho_1, \rho_2, \rho_3)$.

$$\left.\begin{aligned}\rho_1' &= \rho_1 \times x_1 + \rho_2 \times y_1 + \rho_3 \times z_1 \\ \rho_2' &= \rho_1 \times x_2 + \rho_2 \times y_2 + \rho_3 \times z_2 \\ \rho_3' &= \rho_1 \times x_3 + \rho_2 \times y_3 + \rho_3 \times z_3\end{aligned}\right\} \quad (12)$$

Then, the eigenvalues of the Hessian matrix are corrected as shown in Formula (13). Note that the eigenvalues of the evaluation matrix are taken as $\lambda_1$, $\lambda_2$, $\lambda_3$ and $\alpha$ is taken as a predetermined coefficient. Here, $\alpha$ is a predetermined weight designed so as to cancel out one of the response waveforms most that appear at two positions equidistance from the origin of the second order partial differential of solid sphere model function (center of the solid sphere), The weight is designed according to the radius R of the solid sphere and the kernel size s.

$$\left.\begin{aligned}\lambda_1' &= \begin{cases} 0 & \text{if } |\lambda_1| < |\alpha\rho_1'| \\ \min(|\lambda_1 + \alpha\rho_1'|, |\lambda_1 - \alpha\rho_1'|) & \text{otherwise} \end{cases} \\ \lambda_2' &= \begin{cases} 0 & \text{if } |\lambda_2| < |\alpha\rho_2'| \\ \min(|\lambda_2 + \alpha\rho_2'|, |\lambda_1 - \alpha\rho_2'|) & \text{otherwise} \end{cases} \\ \lambda_3' &= \begin{cases} 0 & \text{if } |\lambda_3| < |\alpha\rho_3'| \\ \min(|\lambda_3 + \alpha\rho_3'|, |\lambda_1 - \alpha\rho_3'|) & \text{otherwise} \end{cases}\end{aligned}\right\} \quad (13)$$

In Formula (13), $\lambda_1+\alpha\rho'$ represents a response when a correction for cancelling out one (e.g., the response waveform on the left side of A of FIG. 5A) of the two response waveforms symmetrical with respect to the center of the solid sphere model function is performed in each differential direction. $\lambda_1-\alpha\rho'$ represents a response when a correction for cancelling out the other one (e.g., the response waveform on the right side of A of FIG. 5A) of the two response waveforms. As shown in Formula (13), the eigenvalue $\lambda_1'$ is corrected to a value smaller of the two responses $|\lambda_1+\alpha\rho'|$ and $|\lambda_1-\alpha\rho'|$. As a result, if either one of the $|\lambda_1+\alpha\rho'|$ and $|\lambda_1-\alpha\rho'|$ is small, the value of each eigenvalue $\lambda_1'$ becomes small while the value of each eigenvalue $\lambda_1'$ becomes large only when each of the $|\lambda_1+\alpha\rho'|$ and $|\lambda_1-\alpha\rho'|$ is large. The same is true for $\lambda_2'$ and $\lambda_3'$.

In the case where a structure is erroneously detected by the conventional method, that is, in the case where a response is obtained only one of the two response waveforms symmetrical with respect to the center of the solid sphere model function, if either one of, the responses of the solid sphere model function is cancelled out according to the present invention, at least one of the values of the $|\lambda_1+\alpha\rho'|$ and $|\lambda_1-\alpha\rho'|$ becomes small and the value min ($|\lambda_1+\alpha\rho'|$, $|\lambda_1-\alpha\rho'|$) becomes small. On the other hand, in the case where a structure is correctly detected, that is, in the case where two opposite portions of the contour of a structure (both ends of a line segment traversing the structure) in an image correspond respectively to the two positions where the response waveforms of the second order partial differential of the solid sphere model function are indicated with respect to each differential direction, even when either one of the two response waveforms symmetrical with respect to the center of the solid sphere model function, a large response may be obtained based on the other response waveform, so that the minimum value of the two responses $|\lambda_1+\alpha\rho'|$ and $|\lambda_1-\alpha\rho'|$ becomes large. Therefore, the case where a structure is erroneously detected, that is, the case where the response is obtained only for either one of the two response waveforms may be discriminated and structures may be discriminated accurately. Formula (13) illustrates an example case where the correction is performed using the absolute values of the responses, but the correction may performed without using the absolute values. Further, the discrimination of a target structure may be made by using the $\lambda_1+\alpha\rho'$ and $\lambda_1-\alpha\rho'$ separately without using the min ($|\lambda_1+\alpha\rho'|$, $|\lambda_1-\alpha\rho'|$).

Then, the evaluation unit 34 uses corrected eigenvalues $\lambda_1'$, $\lambda_2'$, $\lambda_3'$ instead of the eigenvalues $\lambda_1$, $\lambda_2$, $\lambda_3$ in Formulae (14) and (15) given below and, using the values $R_A$, $R_B$, $R_C$ calculated by this, calculates an evaluation value L0 (lineness) of line-like structureness and the evaluation value P0 (planeness) of plane-like structureness at each pixel of the three-dimensional multiple resolution image Msi. As described above, the evaluation unit 34 may discriminate a point-like structure, a line-like structure, and a plane-like structure based on the corrected eigenvalues $\lambda_1'$, $\lambda_2'$, $\lambda_3'$ of the Hessian matrix and eigenvectors $e_1$, $e_2$, $e_3$, but it is not necessarily to evaluate all of the point-like structure, line-like structure, and plane-like structure, and may perform discrimination for only some of the point-like structure, line-like structure, and plane-like structure according to the requirements of the specifications. As the present embodiment intends to extract a line-like structure and a plane-like structure from a medical image, evaluation values are calculated only for the line-like structure and the plane-like structure.

$$L0(\text{Lineness}) = \left(1 - \exp\left(-\frac{R_A^2}{2a^2}\right)\right)\exp\left(-\frac{R_B^2}{2b^2}\right)\left(1 - \exp\left(-\frac{S_{2nd}^2}{2c^2}\right)\right) \quad (14)$$

-continued $$P0(\text{Planeness}) = \exp\left(-\frac{R_A^2}{2e^2}\right)\exp\left(-\frac{R_C^2}{2f^2}\right)\left(1-\exp\left(-\frac{S_{2nd}^2}{2g^2}\right)\right) \quad (15)$$

Note that a to h in Formulae (14) and (15) are constants. Further, $R_A$, $R_B$, $R_C$ are calculated by Formulae (16) to (19) given below. Still further, $S_{2nd}$ is the power of the second order partial differential value and calculated by Formula (19) given below.

$$R_A = \frac{|\lambda_2|}{|\lambda_3|} \quad (16)$$

$$R_B = \frac{|\lambda_1|}{\sqrt{\lambda_2 \lambda_3}} \quad (17)$$

$$R_C = \frac{\sqrt{\lambda_1 \lambda_2}}{|\lambda_3|} \quad (18)$$

$$S_{2nd} = \sqrt{\lambda_1^2 + \lambda_2^2 + \lambda_3^2} \quad (19)$$

Figure 6A:
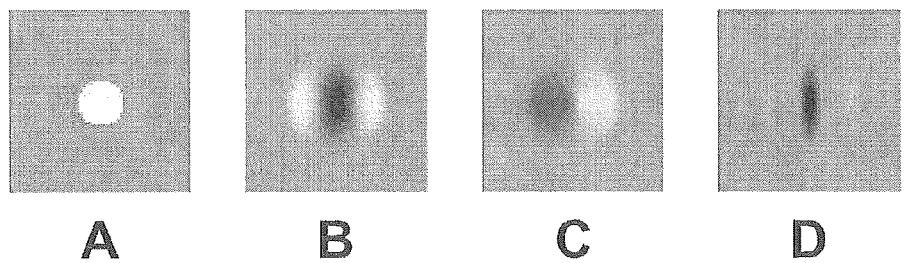
FIG. 6A is a drawing for explaining response after performing the correction processing according to the first embodiment of the present invention (case where the size of the structure corresponds to the size of the solid sphere represented by the solid sphere mode function).
Figure 6B:
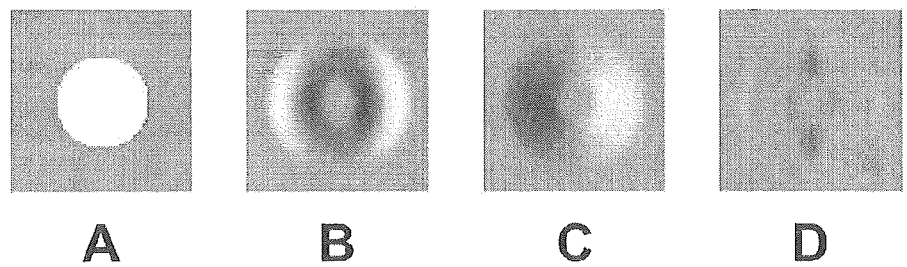
FIG. 6B is a drawing for explaining response after performing the correction processing according to the first embodiment of the present invention (case where the size of the solid sphere represented by the solid sphere model function is greater than the size of the structure).

An example response obtained by performing correction processing on a sample image representing a line-like structure by the correction unit 33 after filtering processing by the filtering unit 32 will be illustrated using FIGS. 6A and 6B. FIG. 6A is a drawing for explaining a response in the case where the size of the structure (length of a line segment traversing the structure) substantially corresponds to the size of the solid sphere model function (diameter of the solid sphere). A of FIG. 6A shows an X-y plan view of luminance values of the line-like structure. B of FIG. 6A shows an x-y plan view of a response obtained by performing filtering processing on the image data of A of FIG. 6A using the second order partial differential of the solid sphere model function in x direction. C of FIG. 6A shows an x-y plan view of a response obtained by performing filtering processing on the image data of A of FIG. 6A using the first order partial differential of the hollow sphere model function in x direction. D of FIG. 6A shows an x-y plan view of a response obtained by performing filtering processing on the image data of A of FIG. 6A using the second order partial differential of the solid sphere model function in x direction corrected using the response obtained by the first order partial differential filtering of the hollow sphere in x direction.

As shown in D of FIG. 6A, a peak of line-like structureness appears near the center of the line-like structure, and it is known that a favorable response for discriminating a line-like structure is obtained by the image processing according to the present embodiment.

FIG. 6B is a drawing for explaining a response in the case where the size of a structure in x direction (length of a line segment traversing the structure) is greater than the diameter of the solid sphere of the solid sphere model function. A of FIG. 6B shows an X-y plan view of luminance values of the line-like structure. B of FIG. 63 shows an x-y plan view of a response obtained by performing filtering processing on the image data of A of FIG. 6B using the second order partial differential of the solid sphere model function in x direction. C of FIG. 6B shows an x-y plan view of a response obtained by performing filtering processing on the image data of A of FIG. 6B using the first order partial differential of the hollow sphere model function in x direction. D of FIG. 6B shows an x-y plan view of a response obtained by performing filtering processing on the image data of A of FIG. 6B using the second order partial differential of the solid sphere model function in x direction corrected using the response obtained by the first order partial differential filtering of the hollow sphere in x direction.

Whereas, B of FIG. 6B that shows an evaluation value corresponding to the method of M. Law and A. Chung, "Three Dimensional Curvilinear Structure Detection Using Optimally Oriented Flux", Proceedings of ECCV, pp. 368-382, 2008, certain responses appear at two positions (two negative peaks) which causes erroneous discrimination, D of FIG. 6B that shows a response obtained by the method of the present embodiment, the response is very weak and it is known that the response that causes erroneous discrimination is suppressed.

D of FIGS. 6A and D of FIG. 6B show responses when an element (Ixx) of the Hessian matrix shown in Formula (1) is applied instead of $\lambda_1$ of Formula (13). The processing for calculating the eigenvalues performs only linear transform of the space in Hessian matrix and does not influence on the value of the response. Therefore, instead of the eigenvalue $\lambda_1$ obtained by performing eigenvalue analysis on the Hessian matrix in Formula (13) described above, correction of the element of the Hessian matrix before being subjected to eigenvalue analysis allows the effect of cancelling out the response that causes erroneous detection to be observed by the corrected element.

In the present embodiment, an evaluation value L0 of line-like structureness and an evaluation value P0 of plane-like structureness are calculated in three-dimensional multiple resolution images Msi having different resolutions. The calculated evaluation values L0, P0 serve as evaluation values at a corresponding pixel position of the original three-dimensional image M0, but the evaluation values are calculated at corresponding pixel positions of all of the three-dimensional multiple resolution images Msi.

The segmentation unit 40 segments a blood vessel region and the region other than the blood vessel region of the three-dimensional image M0 based on the evaluation value L0 of line-like structureness and the evaluation value P0 of plane-like structureness calculated by the discrimination unit 30. More specifically, the blood vessel region is set as a target region while the region other than the blood vessel region is set as a background region, then a discrimination region of a predetermined pixel size is set at all pixel positions within the three-dimensional image M0, and the discrimination regions are divided into target regions and background regions using a graph cut segmentation method. The graph cut segmentation method is described in Y. Y. Boykov and M. Jolly, "Interactive Graph Cuts for Optimal Boundary & Region Segmentation of Objects in N-D Images", Proceedings of "International Conference on Computer Vision", vol. I, pp. 105-112, 2001. In the present embodiment, the segmentation unit 40 segments the blood vessel region and the region other than the blood vessel region of the three-dimensional image M0 by the method which is the same as the method described in Japanese Unexamined Patent Publication No. 2011-206531, which is a past application by the present inventor, based on the evaluation value L0 of line-like structureness and evaluation value P0 of plane-like structureness calculated by the discrimination unit 30.

The display unit 50 is a monitor, a CRT screen, or the like that displays a two-dimensional image, a three-dimensional image, and the like. In the present embodiment, a line-like structure or a plane-like structure may be overviewed and the continuity thereof may be visualized by performing a volume rendering display of the line-like structure segmented as the target region on the display unit 50.

The input unit 60 includes a key board, a mouse, and the like.

Next, processing performed in the present embodiment will be described. FIG. 7 is a flowchart of processing performed in the present embodiment. First, the image obtaining unit 10 generates a three-dimensional image M0 from two dimensional images captured by the X-ray CT system 2 (step ST1). Then, the detection region setting unit 20 makes the three-dimensional image M0 isotropic and generates a plurality of three-dimensional multiple resolution images Msi having different resolutions by performing a multiple resolution transformation on the three-dimensional image M0 (step ST2).

Next, the filtering unit 32 of the discrimination unit 30 performs filtering on each of the three-dimensional multiple resolution images Msi using second order partial differential of a solid sphere model function and a Gaussian kernel function and calculates a Hessian matrix at each pixel position (step ST3). Then, the correction unit 33 corrects an eigenvalue of the aforementioned Hessian matrix using a first order partial differential vector of the hollow sphere model function (step ST4). Next, the evaluation unit 34 calculates an evaluation value L0 of line-like structureness and an evaluation value P0 of plane-like structureness based on the corrected eigenvalue and the eigenvector (step ST5).

Next, the segmentation unit 40 divides the three-dimensional image M0 into a target region (blood vessel region) and a background region using the aforementioned graph cut segmentation method (step ST6). Then, the display unit 50 performs a volume rendering display of the divided target region and the background region (step ST7) and the processing is completed.

Figure 8A:
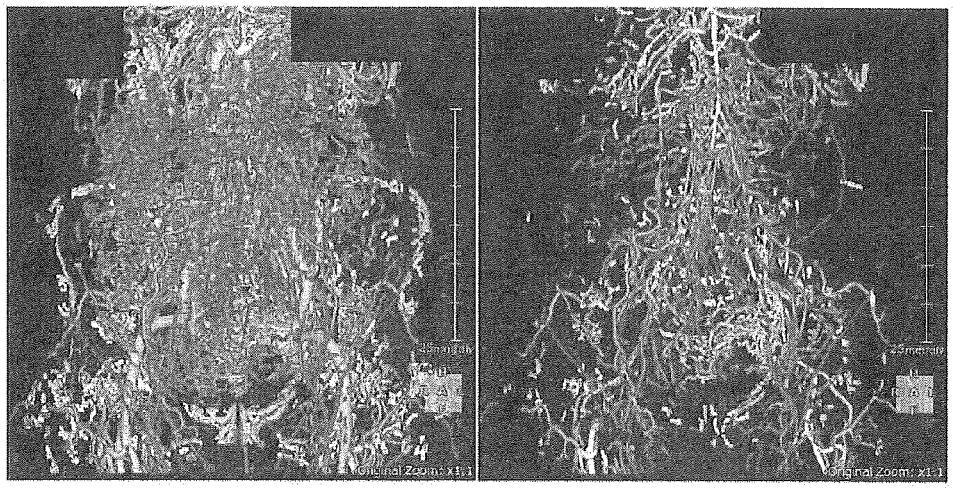
FIG. 8A is an example in which the image processing according to the first embodiment of the present invention is applied to blood vessel extraction (pseudo three-dimensional image).
Figure 8B:
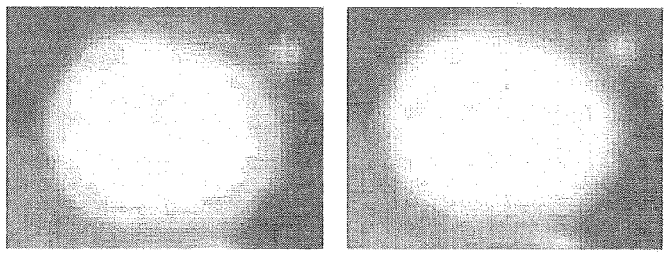
FIG. 8B is an example in which the image processing according to the first embodiment of the present invention is applied to blood vessel extraction (tomographic image).

Examples in which the image processing of the present embodiment is applied to blood vessel discrimination in a chest CT image of an actual patient and the conventional method is applied to blood vessel discrimination in the same CT image are shown in FIGS. 8A and 8B. In FIGS. 8A and 8B, application examples of the conventional image processing (comparative examples) are shown on the left and application examples of the present embodiment are shown on the right. FIG. 8A shows pseudo three-dimensional images in which discriminated blood vessel regions are rendered by a volume rendering method while FIG. 8B represents a portion of FIG. 8A in an enlarged axial tomographic image.

As shown in FIG. 8A, the conventional method displays many blood vessels due to erroneous discrimination while in the application example of the present embodiment, it is known that erroneous discrimination is largely suppressed and blood vessels are extracted accurately. Further, in the comparative example (left) in FIG. 8B, a portion which is erroneously discriminated as being likely a line-like structure is shown in light gray inside of the blood vessel, but in the application example of the present embodiment (right), it is known that the portion erroneously discriminated as being likely a line-like structure inside of the blood vessel (light gray portion) is not observed.

As described above, according to the present embodiment, first order partial differential vectors of a function having a response waveform at the same position as the position of one response waveform of the second order partial differential of a solid sphere model function which is substantially identical in shape to the one response waveform with a reversed positive/negative sign is calculated, and a correction is made such that, of the response waveforms of the second order partial differential of the solid sphere model function in each direction which appear at two positions symmetrically separated with respect to the center of the solid sphere, a response waveform appearing at one position is cancelled out using values obtained by projecting the first order partial differential vectors onto the directions of the Hessian matrix. This may inhibit erroneous discrimination that occurs when the contour of a structure corresponds to only one position where a response waveform of the second order partial differential of the solid sphere model function in any one of the directions appears and the accuracy of the evaluation values may be improved. Consequently, a structure included in an image may be discriminated more accurately based on the evaluation values. In image filtering processing in Fourier space, it is generally not easy to perform correction to change only a certain undesirable value of the filter coefficients, by focusing attention on the response characteristics of the second order partial differential of the solid sphere model function and using the response characteristics of the first order partial differential of the hollow sphere model function, as in the present embodiment, the problem of erroneous discrimination in the method of A. F. Frangi et al., "Multiscale vessel enhancement filtering", Proceedings of MICCAI, Vol. 1496, pp. 130-137, 1998 may be eliminated.

Further, as the "first order" partial differential vectors of the hollow sphere model function are used for correction in the first embodiment, once the partial differential values in x, y, z directions are calculated, a partial differential value in any direction may be calculated. That is, the use of the "first order" partial differential vectors of the solid sphere model function by projecting onto directions of the eigenvectors of the second order partial differential, the correction of the second order partial differential in any direction is possible. As a result, the increase in the amount of calculation for correction is relatively small and computers with various processing power may be used as the image processing apparatus of the present embodiment.

Further, as the response waveform of the first partial differential of the hollow model function at one position in each direction has a reversed positive/negative sign to the sign of the response waveform at one position of the second partial differential of the solid sphere model function in each direction with a very similar shape, the response waveform at one position of the second order partial differential of the solid sphere model function may be cancelled out favorably.

Still further, in the first embodiment described above, with respect to functions representing solid spheres of a plurality of sizes with radius R, Hessian matrices are calculated, then based on the plurality of Hessian matrices, corrections for suppressing responses that cause erroneous discrimination are made, and evaluation values of line-like structureness and plane-like structureness are calculated at each pixel position. Consequently, a structure of a size corresponding to each solid sphere size may be evaluated properly. In addition, if the target region is segmented based on the evaluation values, as in the first embodiment described above, structures of a plurality of sizes may be segmented properly as the target regions.

As the method for performing Hessian analysis on structures of different sizes, a method that performs Hessian analysis on the images of a plurality of different resolutions by applying a constant kernel size "σ" and a constant radius R of solid sphere model function may be used, as in the present embodiment, or a method that performs Hessian analysis on an image of a constant resolution by applying different constant kernel sizes "σ" and different radii R of solid sphere model functions may be used. For example, it is conceivable that the length of a line segment traversing a detection target structure, such as the long axis and the short axis of the structure, are obtained in advance from experimentally obtained data and the resolution of the three-dimensional multiple resolution image Msi or the kernel size "σ" and the radius R are set such that the length of a line segment traversing a detection target structure corresponds to the size of the radius R.

In the first embodiment described above, both the evaluation value L0 of line-like structureness and the evaluation value P0 of plane-like structureness are calculated, but only either one of the evaluation value L0 of line-like structureness and the evaluation value P0 of plane-like structureness may be calculated.

A second embodiment of the present invention will be described herein below. In the second embodiment, the correction processing differs from the correction processing of the first embodiment but, other than that, the second embodiment is identical to the first embodiment and the function of each functional block is also common. Hereinafter, a description will be made focusing on the difference from the first embodiment and the description for the identical points will be omitted here.

In order to cancel out the response waveform at one position of response waveforms at two positions by the second order partial differential of the solid sphere model function described above, in the second embodiment, the attention is focused on the characteristics that the response waveform of the second order partial differential of the solid sphere model function located on the negative side of the x direction has one positive peak and one adjoining negative peak from the negative side of the x direction, while the response waveform located on the positive side of the x direction has one negative peak and one adjoining positive peak from the negative side of the x direction, and it is found that a response waveform located at the same position as the position of one of the response waveforms with a reversed positive/negative sign to the sign of the one of the waveforms and substantially the same shape as the shape of the one of the waveforms can be generated by combining first order partial differential of a solid sphere model function $f_2(r)$ (second solid sphere model function) of a solid sphere slightly smaller than the solid sphere in each direction and first order partial differential of a solid sphere model function $f_3(r)$ (third solid sphere model function) of a solid sphere slightly larger than the solid sphere in each direction. Note that the solid sphere model function used in filtering processing by the filtering unit 32 is referred to as the first solid sphere model function here for the purpose of distinction.

A of FIG. 9A shows a response of first order partial differential of the second solid sphere model function $f_2(r)$ having a radius $R_2$ in x direction, B of FIG. 9A shows a response of first order partial differential of the third solid sphere model function $f_3(r)$ having a radius $R_3$ in x direction, and C of FIG. 9A shows a response obtained by adding the first order partial differential of the third solid sphere model function $f_3(r)$ in x direction to a first order partial differential obtained by reversing the positive/negative sign of the second solid sphere model function $f_2(r)$ in x direction.

As illustrated in A and B of FIG. 9A, the responses of the first order partial differential of the second and the third solid model functions f2(r) f3(r) have characteristics that they have response waveforms having one positive peak on the negative side of the center of the solid sphere and one negative peak on the positive side of the center of the solid sphere, and each response waveform appears symmetrically with respect to the center.

By combining a first order partial differential obtained by reversing the positive/negative sign of the first order partial differential of the solid sphere model function $f_2(r)$ in x direction shown in A of FIG. 9A with the first order partial differential of the solid sphere model function $f_3(r)$ in x direction shown in B of FIG. 9A, the response in x direction shown in C of FIG. 9A may be obtained. C of FIG. 9A has response waveforms at two positions symmetrical with respect to the center of the solid sphere and the response waveforms have characteristics that the response waveform located on the negative side of x direction has one negative peak and one adjoining positive peak from the negative side of x direction while the response waveform located on the positive side of x direction has one negative peak and one adjoining positive peak from the negative side of x direction.

That is, if the responses of the first order partial differentials of the second and third solid sphere model functions $f_2(r)$ $f_3(r)$ shown in C of FIG. 9A are combined to the filtering by the second order partial differential matrix of the solid sphere model function in each direction, the response waveforms on the positive side in each direction are cancelled out as they have reverse signs at the same position, while the response waveforms on the negative side in each direction are reinforced as they have the same sign at the same position, thereby resulting in that a response waveform appears only at one position on the positive side of x direction, as shown in C of FIG. 5A.

In the present embodiment, in order to cancel out the response waveform at one position of the second order partial differential of the first solid sphere model function, the second radius $R_2$ is the same as the distance from the center of the solid sphere to the positive peak of the response waveform located on the positive direction in the second order partial differential of the first solid sphere model function, while the third radius $R_3$ is the same as the distance from the center of the solid sphere to the negative peak of the response waveform located on the positive direction in the second order partial differential of the first solid sphere model function. With respect to the second radius $R_2$ (third radius $R_3$), "the distance from the center to the positive (negative) peak" may be greater or smaller than the second radius $R_2$ (third radius $R_3$) within the range having an effect of cancelling out the response waveform at one position of the second order partial differential of the aforementioned solid sphere model function in each direction. Preferably, however, the second radius $R_2$ (third radius $R_3$) corresponds strictly to the distance from the center to the positive (negative) peak in order to make the response waveform of combined first order partial differentials of the second and the third solid sphere model functions in each direction correspond more to the response waveform of the second order partial differential of the solid sphere model function, as in the present embodiment.

The responses of the first order differentials of the second and the third solid sphere model functions in x direction will be described with reference to FIG. 9S. A of FIG. 9B shows a response of the first order partial differential of the second solid sphere model function $f_2(r)$ in x direction, B of FIG. 9B shows a response of the first order partial differential of the third solid sphere model function $f_3(r)$ in x direction, and C of FIG. 9B shows a response when the first order partial differential of the solid sphere model function $f_3(r)$ is added to a first order partial differential obtained by reversing the positive/negative sign of the first order partial differential of the second solid sphere model function $f_2(r)$ in x direction. In FIG. 9B, each response described above is shown by a plurality of x-y plan views having different z coordinate values of equal intervals, and the plurality of x-y plan views is arranged in descending order of z coordinate values from the top in the vertical direction. In each of the x-y plan views in FIG. 9B, the higher (whiter) the brightness, the greater the response in the positive direction and the darker (blacker) the brightness, the greater the response in the negative direction.

Figure 9B:
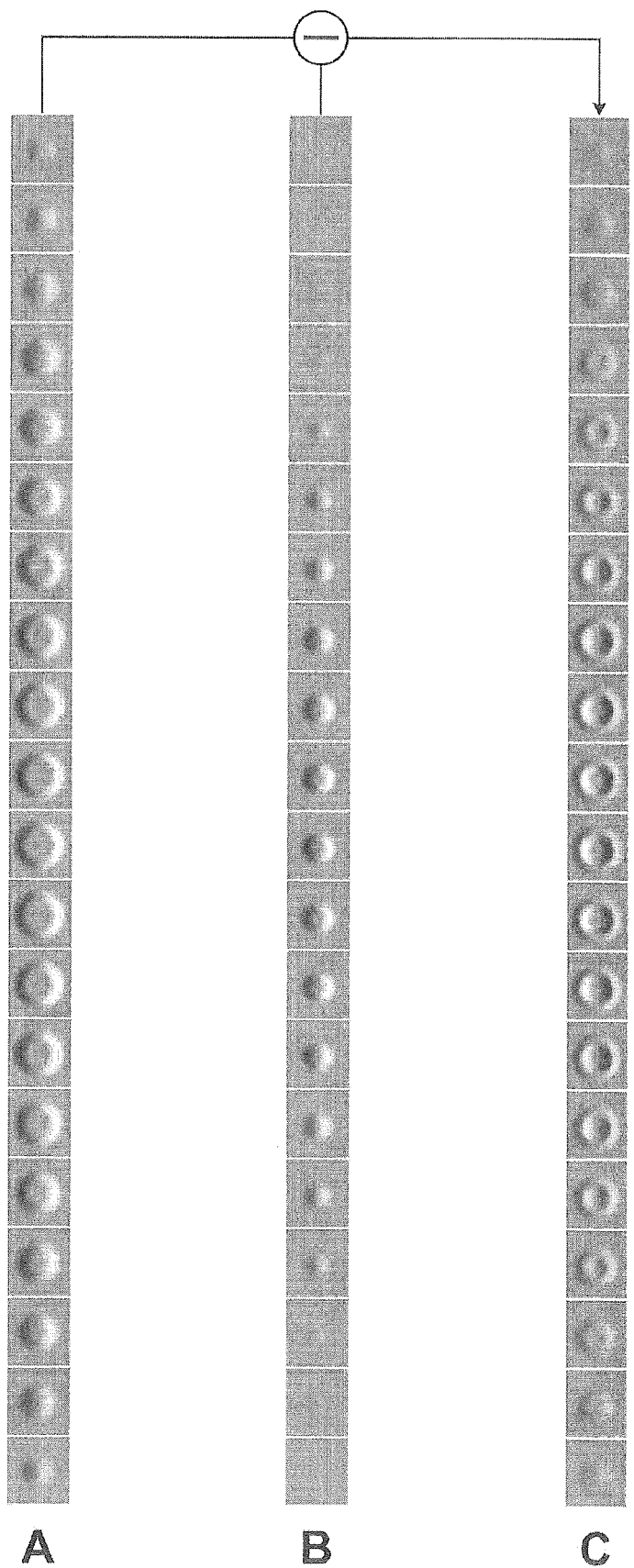
FIG. 9B is a drawing for explaining the principle of correction by first order partial differential vectors of second and third solid sphere model function of the second embodiment of the present invention.

It is known that, in the response waveform on the negative side shown in C of FIG. 9B, the negative peak located on the negative side of the center of the first order partial differential of the second solid sphere model function in x direction shown in A of FIG. 9B and the negative peak located on the negative side of the center of the first order partial differential of the third solid sphere model function in x direction shown in B of FIG. 9B are shifted and overlapped, thereby forming a waveform in which a negative peak and a positive peak are adjoining from the negative direction. Further, it is known that, in the response waveform on the positive side shown in C of FIG. 9B, the positive peak located on the positive side of the center of the first order partial differential of the second solid sphere model function in x direction shown in A of FIG. 9B and the positive peak located on the positive side of the center of the first order partial differential of the third solid sphere model function in x direction shown in B of FIG. 9B are shifted and overlapped, thereby forming a waveform in which a negative peak and a positive peak are adjoining from the negative direction. If the second order partial differential of the first solid sphere model function in x direction shown in B of FIG. 5C by combining the first order partial differentials of the first and the second solid sphere model functions so as to show the response of C of FIG. 9B, the response waveform on the negative side of the center of the solid sphere may be cancelled out, as illustrated in FIG. 53.

In the second embodiment, the correction unit 33 corrects the Hessian matrix such that only the response at one position of the first solid sphere model function f(r) is cancelled out using each first order partial differential of the second and the third solid sphere model functions based on the aforementioned principle. A specific correction method will be described hereinafter.

First, with respect to the solid sphere model function of the second radius $R_2$, the correction unit 33 calculates first order partial differential vectors using the second radius $R_2$ in Formula (2) instead of radius R. In Formula (2), the part $(2\pi v_x)^l \times (2\pi v_y)^m \times (2\pi v_z)^n$ corresponds to the differential processing in Fourier space, and each of first order partial differential vectors $(S_x, S_y, S_z)$ calculated with respect to the second solid sphere model function $f_2(r)$ may be calculated by substituting the coefficients l, m, n corresponding to the respective differential directions to Formula (9) such that l+m+n=1 (0<l, 0<m, 0<n). Likewise, the correction unit 33 calculates the first order partial differential vectors $(t_x, t_y, t_z)$ with respect to the third solid sphere model function $f_3(r)$ by using the third radius $R_3$ in Formula (2) instead of radius R. Then, each of the first order partial differential vectors $(s_x, s_y, s_z)$ calculated with respect to the second solid sphere model function $f_2(r)$ and each of the first order partial differential vectors $(t_x, t_y, t_z)$ calculated with respect to the third solid sphere model function $f_3(r)$ are weight added to calculate $(\rho_1, \rho_2, \rho_3)=(s_x-\beta t_x, s_y-\beta t_y, s_z-\beta t_z)$.

In Formula (2), the filtering is performed in Fourier space, but the filtering may be performed in real space.

As the first order partial differential vectors $(\rho_1, \rho_2, \rho_3)$ of X direction, Y direction, and Z direction calculated in the manner described above are deviated from the directions of the eigenvectors $e_1, e_2, e_3$ of the eigenvalues $\lambda_1, \lambda_2, \lambda_3$, the correction unit 33 calculates first order partial differential vectors $\rho_1', \rho_2', \rho_3'$ corresponding to the directions of the eigenvectors $e_1, e_2, e_3$ by Formula (12) given below.

Then, the eigenvalues of the Hessian matrix are corrected based on Formula (13), as in the first embodiment. Note that the eigenvalues of the evaluation matrix are taken as $\lambda_1, \lambda_2, \lambda_3$ and $\alpha, \beta$ are taken as predetermined coefficients. Here, $\alpha, \beta$ are predetermined weights designed so as to cancel out one of the response waveforms most that appear at two positions equidistance from the origin of the second order partial differential of solid sphere model function (center of the solid sphere). These weights are designed according to the radius R of the solid sphere and the kernel size s.

Then, as in the first embodiment, the evaluation unit 34 uses eigenvalues $\lambda_1', \lambda_2', \lambda_3'$ instead of the eigenvalues $\lambda_1, \lambda_2, \lambda_3$ in Formulae (14) and (15) given below and, using the values $R_A, R_B, R_C$ calculated by this, calculates an evaluation value L0 (lineness) of line-like structureness and the evaluation value P0 (planeness) of plane-like structureness at each pixel of the three-dimensional multiple resolution images Msi.

Also in the second embodiment, as in the first embodiment, first order partial differential vectors of a function (function of combined first order partial differentials of solid sphere model functions of two different sizes) having a response waveform at the same position as the position of one response waveform of the second order partial differential of a solid sphere model function which is substantially identical in shape to the one response waveform with a reversed positive/negative sign is calculated, and a correction is made such that, of the response waveforms of the second order partial differential of the solid sphere model function in each direction which appear at two positions symmetrically separated with respect to the center of the solid sphere, a response waveform appearing at one position is cancelled out using values obtained by projecting the first order partial differential vectors onto the directions of the Hessian matrix. Consequently, as in the first embodiment, erroneous discrimination that occurs when the contour of a structure corresponds to only one position where a response waveform of the second order partial differential of the solid sphere model function in any one of the directions appears to be inhibited, whereby the accuracy of the evaluation values may be improved, although the amount of calculation for correction processing by the correction unit 33 is slightly increased as the second embodiment uses the first order differential of each of the solid sphere model functions of two different sizes in correction while the method of the first embodiment uses the first order differential of the solid sphere model function of one size in correction.

Further, in the second embodiment, the second radius $R_2$ corresponds to the length from the center of the solid sphere to the positive peak or the length from the center of the solid sphere to the negative peak, whichever is longer, while the third radius $R_3$ corresponds to the length from the center of the solid sphere to the positive peak or the length from the center of the solid sphere to the negative peak, whichever is shorter. Therefore, the effect of cancelling out the response waveform more corresponds to one of the response waveforms of the first solid sphere in which the positive peak and the negative peak are adjoining, and this may preferably realize suppression of the response waveform that causes erroneous discrimination.

Also in the second embodiment, it is preferable that, with respect to functions representing the solid sphere with radius R in a plurality of sizes, Hessian matrices are calculated, then based on the plurality of Hessian matrices, corrections to suppress responses that cause erroneous discrimination are made, and evaluation values of line-like structureness and plane-like structureness are calculated at each pixel position. In this case, a structure of a size corresponding to each kernel size may be evaluated properly. For that purpose, the image processing of the second embodiment may be performed on images of a plurality resolutions using the first solid sphere model function with the constant radius R or the image processing of the second embodiment may be performed on an image of one resolution by changing the first radius R and using the first solid sphere model functions of a plurality of sizes of first radius R.

The image processing method according to each embodiment described above is applicable to the following image processing apparatus for direction discrimination. For example, the image processing apparatus for direction discrimination may be configured not to include the segmentation unit 40, the evaluation unit 34, and the display unit 50 in the first embodiment, but to include a direction discrimination unit instead. As an example of such processing apparatus, the direction discrimination unit may be configured in the following manner with the image obtaining processing performed by the image obtaining unit 10, the detection region setting processing performed by the detection region setting unit 20, and the filtering processing performed by the filtering unit 32 being identical to those of the first embodiment and the function of each functional block also being common.

The direction discrimination unit calculates eigenvalues and eigenvectors $e_1, e_2, e_3$ by performing eigenvalue analysis on the evaluation matrix calculated by the filtering unit 32, and discriminates a principal axis direction of a line-like structure or a normal direction of a plane-like structure based on the directions of the calculated eigenvectors. More specifically, the direction discrimination unit obtains $\lambda_1, \lambda_2, \lambda_3$ and eigenvectors $e_1, e_2, e_3$ of the Hessian matrix obtained by the filtering unit 32 and discriminates the direction pointed by the eigenvector $e_1$ corresponding to the eigenvalue $\lambda_1$ as the axis direction of the line-like structure, if the relationship indicated in Formula (6) is satisfied and, if the relationship indicated in Formula (7) is satisfied, discriminates the direction pointed by the eigenvector $e_2$ corresponding to the eigenvalue $\lambda_2$ as the normal direction of the plate-like structure. Note that the direction discrimination unit may discriminate only either one of the axis direction of a line-like structure according to Formula (6) and the normal direction of a plane-like structure according to Formula (7) based on the eigenvalues and the eigenvectors of the Hessian matrix.

The axis direction of a line-like structure and the normal direction of a plane-like structure obtained by such an image processing apparatus for direction discrimination as described above may be used, for example, as the axis direction when generating a CPR (Curved Planar Reformation/Reconstruction) image of a tubular structure, such as a blood vessel, a large intestine, or the like, reconstructed from a three-dimensional image by the CPR method, and are favorably used in various types of known processing that requires the axis direction of a line-like structure and the normal direction of a plane-like structure. The axis direction of a line-like structure and the normal direction of a plane-like structure obtained by the present invention may be used for various types of known CPR image generation methods, including, for example, A. Kanitsar et al., "CPR—Curved Planar Reformation", IEEE Visualization, 2002.

As the image is a medical image and the structure is a blood vessel in each embodiment described above, the accuracy of discrimination of structures in medical images, in which erroneous discrimination has occurred many times due to the inclusion of blood vessels of various diameters, may be improved significantly.

Further, in each embodiment described above, the filtering unit performs filtering using a second order partial differential matrix of a function representing a solid sphere and filtering using a first order partial differential matrix of a function representing a solid sphere in Fourier space, which is preferable as the processing cost and processing speed may be reduced in comparison with the case where the filtering is performed in real space. But, the filtering unit may perform filtering using a second order partial differential matrix of a function representing a solid sphere, filtering using a first order partial differential matrix of a function representing a solid sphere, and filtering using a first order partial differential matrix of a function representing a hollow sphere in real space.

As described in each aforementioned embodiment, the evaluation unit may discriminate at least one of the point-like local structure, line-like local structure, and plane-like local structure of a structure based on eigenvectors and corrected eigenvalues. Note that the eigenvectors and the eigenvalues, however, may be used to discriminate a structure of any shape, as well as the point-like structure, line-like structure, and plane-like structure.

In each embodiment described above, discrimination of blood vessel is described as an example of line-like structure, but the discrimination method may also be applied to the other like-like structures, such as bronchus and the like. Further, the discrimination method may also be applied not only to bone but also to the other plane-like structures, such as skin, interlobar membrane, and the like.

In each embodiment described above, each evaluation processing or direction discrimination processing is performed with a line-like structure and a plane-like structure included in a three-dimensional image M0 as targets, but each evaluation processing or direction discrimination processing may be performed with a line-like structure and a plane-like structure included in a two-dimensional image as targets.

Further, in each embodiment described above, a line-like structure and a plane-like structure are segmented using a graph cut segmentation method but, of course, other segmentation methods, such as the watershed algorithm and the like, may also be used. The watershed algorithm is a method of segmenting an image like, when water is filled in a terrain in which pixel value information of the image is regarded as height, a boundary is formed between water accumulated in different depressions. Therefore, the line-like structure and the plane-like structure may be segmented by performing appropriate smoothing processing on the evaluation values L0 and P0 of the three-dimensional image M0 and implementing the watershed algorithm.

It should be appreciated that each embodiment described above is for illustration purposes only, and any of the above descriptions should not be used to interpret the technical scope of the present invention in a limited way.

In addition, various modifications made to the system configurations, hardware configurations, processing flows, module organizations, user interfaces, specific processing contents, and the like of the embodiments described above without departing from the spirits of the present invention are included in the technical scope of the present invention.

What is claimed is:

1. An image processing apparatus, comprising:
   a filtering unit that performs filtering on each pixel position in an image using a second order partial differential of a function representing a solid sphere and calculates a Hessian matrix; and
   an evaluation unit that discriminates a structure included in the image using eigenvalues and eigenvectors obtained by performing eigenvalue analysis on the calculated Hessian matrix,
   wherein the filtering unit includes a correction unit that performs filtering on each pixel position in the image using a first order partial differential of a function representing a hollow sphere having the same radius as the radius of the solid sphere and obtains first order partial differential vectors, and carries out correction to cancel out one of response waveforms of the second order partial differential of the function representing the solid sphere in each direction, the response waveforms appearing at two positions symmetrically separated with respect to the center of the solid sphere, using values obtained by projecting the obtained first order partial differential vectors onto directions of the eigenvectors.

2. The image processing apparatus as claimed in claim 1, wherein, if eigenvalues of the Hessian matrix are taken as $\lambda_1$, $\lambda_2$, $\lambda_3$, eigenvectors are taken as $e_1=(x_1, y_1, z_1)$, $e_2=(x_2, y_2, z_2)$, $e_3=(x_3, y_3, z_3)$, and the first order partial differential vectors of the function representing the hollow sphere are taken as $(\rho_1, \rho_2, \rho_3)$, the correction unit carries out the correction to cancel out the one of the response waveforms by correcting the eigenvalues as shown in Formula (13) given below using $\rho_1'$, $\rho_2'$, $\rho_3'$ calculated by Formula (12) given below and a predetermined coefficient:

$$\left.\begin{aligned} \rho_1' &= \rho_1 \times x_1 + \rho_2 \times y_1 + \rho_3 \times z_1 \\ \rho_2' &= \rho_1 \times x_2 + \rho_2 \times y_2 + \rho_3 \times z_2 \\ \rho_3' &= \rho_1 \times x_3 + \rho_2 \times y_3 + \rho_3 \times z_3 \end{aligned}\right\} \quad (12)$$

$$\lambda_1' = \begin{cases} 0 & \text{if } |\lambda_1| < |\alpha\rho_1'| \\ \min(|\lambda_1 + \alpha\rho_1'|, |\lambda_1 - \alpha\rho_1'|) & \text{otherwise} \end{cases}$$

$$\lambda_2' = \begin{cases} 0 & \text{if } |\lambda_2| < |\alpha\rho_2'| \\ \min(|\lambda_1 + \alpha\rho_2'|, |\lambda_1 - \alpha\rho_2'|) & \text{otherwise} \end{cases} \quad (13)$$

$$\lambda_3' = \begin{cases} 0 & \text{if } |\lambda_3| < |\alpha\rho_3'| \\ \min(|\lambda_3 + \alpha\rho_3'|, |\lambda_1 - \alpha\rho_3'|) & \text{otherwise} \end{cases}$$

3. The image processing apparatus as claimed in claim 1, wherein the function representing the hollow sphere is represented by Formula (10) given below:

$$\left.\begin{aligned} f_1(r) &= \delta(r - R_4) \\ r &= \sqrt{x^2 + y^2 + z^2} \end{aligned}\right\} \quad (10)$$

where, x, y, z are the coordinates of three-dimensional space, r is the polar coordinate representation thereof, and $R_4$ is the radius of the hollow sphere.

4. The image processing apparatus as claimed in claim 1, wherein the filtering unit calculates, with respect to functions representing the solid sphere in a plurality of sizes, the Hessian matrix by performing filtering with a second order partial differential matrix of a function representing each solid sphere.

5. The image processing apparatus as claimed in claim 1, wherein the filtering unit performs the filtering using the second order partial differential matrix of the function representing the solid sphere in Fourier space.

6. The image processing apparatus as claimed in claim 1, wherein the evaluation unit discriminates at least one of local point-like, line-like, and plane-like structures of the structure.

7. The image processing apparatus as claimed claim 1, wherein the image is a medical image and the structure is a blood vessel.

8. An image processing apparatus, comprising:
a filtering unit that performs filtering on each pixel position in an image using a second order partial differential of a function representing a first solid sphere and calculates a Hessian matrix; and
an evaluation unit that discriminates a structure included in the image using eigenvalues and eigenvectors obtained by performing eigenvalue analysis on the calculated Hessian matrix,
wherein the filtering unit includes a correction unit that performs filtering on each pixel position in the image using a first order partial differential of a function representing a second solid sphere having a second radius greater than a first radius which is the radius of the first solid sphere and calculates first order partial differential vectors, further performs filtering on each pixel position in the image using a first order partial differential of a function representing a third solid sphere having a third radius smaller than the first radius and calculates first order partial differential vectors, and carries out correction to cancel out a response waveform at one position of response waveforms of the second order partial differential of the function representing the first solid sphere in each direction, the response waveforms appearing at two positions symmetrically separated with respect to the center of the first solid sphere, using values obtained by projecting the first order partial differential vectors of the function representing the second solid sphere onto directions of the eigenvectors and values obtained by projecting the first order partial differential vectors of the function representing the third solid sphere onto directions of the eigenvectors.

9. The image processing apparatus as claimed in claim 8, wherein:
the response waveform at the one position is a waveform in which one positive peak and one negative peak are adjoining to each other;
the second radius corresponds to the length from the center of the first solid sphere to the positive peak or the length from the center of the first solid sphere to the negative peak, whichever is longer; and
the third radius corresponds to the length from the center of the first solid sphere to the positive peak or the length from the center of the first solid sphere to the negative peak, whichever is shorter.

10. The image processing apparatus as claimed in claim 8, wherein the filtering unit calculates, with respect to functions representing the first solid sphere in a plurality of sizes, the Hessian matrix by performing filtering with a second order partial differential matrix of a function representing each of the first solid spheres.

11. The image processing apparatus as claimed in claim 8, wherein the filtering unit performs the filtering using the second order partial differential matrix of the function representing the first solid sphere in Fourier space.

12. The image processing apparatus as claimed in claim 8, wherein the evaluation unit discriminates at least one of local point-like, line-like, and plane-like structures of the structure.

13. The image processing apparatus as claimed claim 8, wherein the image is a medical image and the structure is a blood vessel.

14. An image processing method, comprising:
a filtering step that performs filtering on each pixel position in an image using a second order partial differential of a function representing a solid sphere and calculates a Hessian matrix; and
an evaluation step that discriminates a structure included in the image using eigenvalues and eigenvectors obtained by performing eigenvalue analysis on the calculated Hessian matrix,
wherein the filtering step performs filtering on each pixel position in the image using a first order partial differential of a function representing a hollow sphere having the same radius as the radius of the solid sphere and obtains first order partial differential vectors, and carries out correction to cancel out one of response waveforms of the second order partial differential of the function representing the solid sphere in each direction, the response waveforms appearing at two positions symmetrically separated with respect to the center of the solid sphere, using values obtained by projecting the obtained first order partial differential vectors onto directions of the eigenvectors.

15. A non-transitory computer readable recording medium on which is recorded an image processing program that causes a computer to perform:

a filtering step that performs filtering on each pixel position in an image using a second order partial differential of a function representing a solid sphere and calculates a Hessian matrix; and an evaluation step that discriminates a structure included in the image using eigenvalues and eigenvectors obtained by performing eigenvalue analysis on the calculated Hessian matrix, wherein the filtering step performs filtering on each pixel position in the image using a first order partial differential of a function representing a hollow sphere having the same radius as the radius of the solid sphere and obtains first order partial differential vectors, and carries out correction to cancel out one of response waveforms of the second order partial differential of the function representing the solid sphere in each direction, the response waveforms appearing at two positions symmetrically separated with respect to the center of the solid sphere, using values obtained by projecting the obtained first order partial differential vectors onto directions of the eigenvectors.

* * * * *